United States Patent
West

(10) Patent No.: US 12,235,256 B2
(45) Date of Patent: Feb. 25, 2025

(54) FORECASTING OF DISINFECTION BYPRODUCTS

(71) Applicant: AMS Trace Metals, Inc., Wilmington, DE (US)

(72) Inventor: Michael J. West, San Jose, CA (US)

(73) Assignee: AMS Trace Metals, Inc., Wilmington, DE (US)

( * ) Notice: Subject to any disclaimer, the term of this patent is extended or adjusted under 35 U.S.C. 154(b) by 1306 days.

(21) Appl. No.: 16/078,845

(22) PCT Filed: Mar. 6, 2017

(86) PCT No.: PCT/US2017/020997
§ 371 (c)(1),
(2) Date: Aug. 22, 2018

(87) PCT Pub. No.: WO2017/155896
PCT Pub. Date: Sep. 14, 2017

(65) Prior Publication Data
US 2019/0056371 A1    Feb. 21, 2019

Related U.S. Application Data

(60) Provisional application No. 62/304,929, filed on Mar. 7, 2016.

(51) Int. Cl.
*G01N 33/18* (2006.01)
*G01N 35/00* (2006.01)
*G01N 35/10* (2006.01)

(52) U.S. Cl.
CPC ... *G01N 33/1826* (2013.01); *G01N 35/00871* (2013.01); *G01N 33/184* (2024.05);
(Continued)

(58) Field of Classification Search
None
See application file for complete search history.

(56) References Cited

U.S. PATENT DOCUMENTS 5,358,875 A    10/1994  Goswami
5,547,877 A    8/1996   Friedman
(Continued)

FOREIGN PATENT DOCUMENTS

CN    101952704 A    1/2011
JP    2008145163 A    6/2008
(Continued)

OTHER PUBLICATIONS

Liu et al., DBP Formation in Hot and Cold Water Across a Simulated Distribution System: Effect of Incubation Time, Heating Time, pH, Chlorine Dose, and Incubation Temperature, 2013, Environ.Sci.Technol., 47, p. 11584-11591. (Year: 2013).*

(Continued)

*Primary Examiner* — Lore R Jarrett
(74) *Attorney, Agent, or Firm* — Marc P. Schuyler

(57) ABSTRACT

Formation potential for disinfection by-products (DBPs) is determined in-situ using one or more automated sample extraction and measurement mechanisms. In one embodiment, such an in-situ mechanism is used to take periodic water samples and measure trihalomethane (THM) concentration in near real-time (i.e., less than two hours), using a measurement process based on modified Fujiwara chemistry. During the extraction and measurement process, water samples can be heated according to a specific temperature/time profile in order to artificially accelerate age of the water sample, so as to cause DBPs to form prematurely. A water monitoring network can monitor detected DBP levels and take automated response actions according to predefined computer policies or rules.

26 Claims, 8 Drawing Sheets

(52) U.S. Cl.
CPC .............. *G01N 2035/00356* (2013.01); *G01N 2035/00881* (2013.01); *G01N 2035/0097* (2013.01); *G01N 2035/1062* (2013.01); *Y02A 20/20* (2018.01)

(56) References Cited

U.S. PATENT DOCUMENTS

| | | | |
|---|---|---|---|
| 8,076,652 B2 * | 12/2011 | Emmert | ................ G01N 30/96 73/61.56 |
| 8,616,051 B2 | 12/2013 | Kimour | |
| 9,134,290 B2 | 9/2015 | Saini | |
| 9,222,921 B2 | 12/2015 | Saini et al. | |
| 9,581,578 B1 * | 2/2017 | Emmert | ............ G01N 33/1826 |
| 9,903,844 B2 | 2/2018 | Saini et al. | |
| 10,018,567 B2 | 6/2018 | Saini | |
| 2003/0092196 A1 | 5/2003 | Saini et al. | |
| 2004/0060372 A1 * | 4/2004 | Hopkins | ............... G01L 1/2243 73/862.637 |
| 2006/0210440 A1 | 9/2006 | Potyrailo et al. | |
| 2010/0204924 A1 | 8/2010 | Wolfe et al. | |
| 2013/0029427 A1 * | 1/2013 | Saini | ................. G01N 33/1826 436/125 |
| 2015/0293070 A1 | 10/2015 | Emmert | |

FOREIGN PATENT DOCUMENTS

| | | |
|---|---|---|
| JP | 2008241606 A | 10/2008 |
| JP | 2009014382 A | 1/2009 |
| WO | 2011133383 A | 10/2011 |
| WO | 2012158388 A | 11/2012 |
| WO | 2017155896 A | 9/2017 |

OTHER PUBLICATIONS

Liu et al., DBP Formation in Hot and Cold Water Across a Simulated Distribution System: Effect of Incubation Time, Heating Time, pH, Chlorine Dose, and Incubation Temperature, 2013, Environ.Sci.Technol., 47, Supplementary Material (9 pages). (Year: 2013).*

Wang et al., "continuous on-line monitoring of haloacetic acids via membrane extraction," Journal of Chromatography A, 1089 (2005) 39-44.

EP Search Report for EP application 11772452-6, mailed Aug. 12, 2014, 6 pages.

PCT/US2011/032438, ISR-WO, 10 pages, mailed Dec. 20, 2011 (ISR-WO for international stage of parent, U.S. Pat. No. 9,134,290).

"Seasonal variations of trihalomethanes (THMs) in water distribution networks of Istanbul City," Desalination 176 (2005) 127-141, 0011-9164/05, 15 pages.

"Investigation of bromide ion effects on disinfection by-products formation and speciation in an Istanbul water supply," Uyak et al., Journal of Hazardous Materials 149 (2007) 445-451, 7 pages, Apr. 7, 2007.

"Seasonal variations of disinfection by-product precursors profile and their removal through surface water treatment plants," Uyak et al., Scients of the Total Environment, 390 (2008) 417-424, Nov. 13, 2007, 8 pages.

"THMs assessment in Khuzestan rural water treatment plants," Ahmadi et al., International Journal of Environmental Health Engineering, V1:6, Jun. 2012, pp. 39-43.

"Field and material-specific simulated distribution system testing as aids to understanding trihalomethane formation in distribution systems," Brereton et al., Can. J. Civ. Eng. 29: 17-26 (2002), pp. 17-27.

"Modeling trihalomethane formation for Jabal Amman water supply in Jordan," Al-Omari et al., Environmental Modeling and Assessment 9: 245-252, 2004.

Wang et al., "Microfluidic supported liquid membrane extraction," May 10, 2005, Analytica Chimica Acta 2005 92-98.

Carrero et al., "Analysis of haloacetic acid mixtures by HPLC using an electrochemical detector coated with a surfactantnafion film," Talanta 1999, 48, pp. 711-718.

Dionex, "Acclaim polar advantage HPLC Columns," 2003, copy obtained on Jan. 22, 2015, pp. 1-8.

Esp@cenet English abstract of Japanese application No. JP2013092520 (A) for Measurement Method and Measurement Device for Haloacetic Acid.

Esp@cenet English abstract of Chinese application No. CN20111398607 for Method for quickly detecting haloacetic acids serving as disinfection byproducts in drinking water.

PCT/US2017/020997, ISR-WO, 10 pages, mailed May 31, 2017.
PCT/US2012/036840, ISR-WO, 12 pages, mailed Nov. 23, 2012.

* cited by examiner

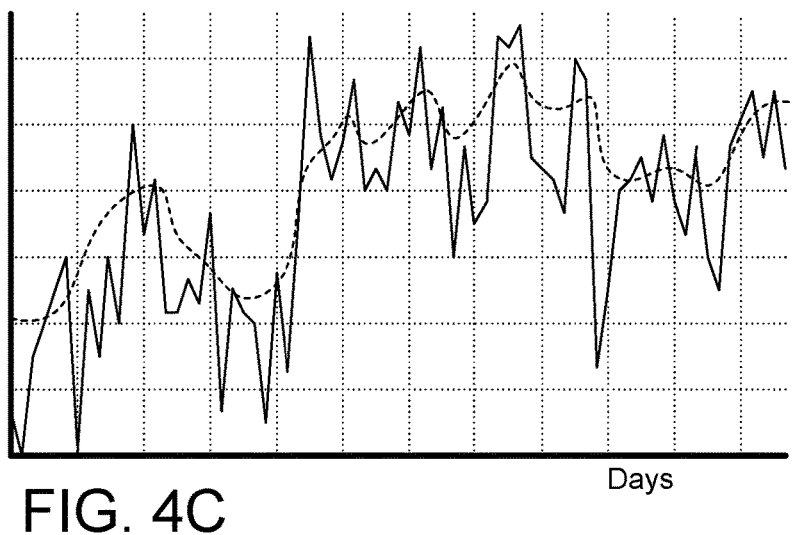
FIG. 4C
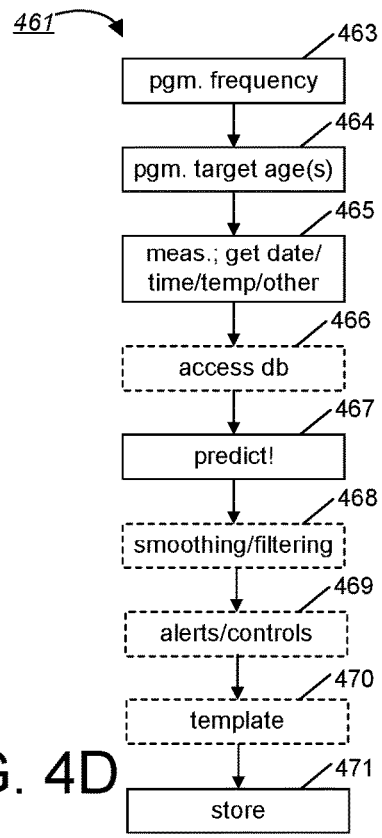
FIG. 4D
| Treatment Plant: (Treated Water) ||
|---|---|
| pH: | 7.3 |
| TOC: | 0.90 mg/L |
| Cl₂ dose at WTP: | 0.90 mg/L |
| Bromide: | 0.10 mg/L |
| TTHM: | 5-25 µg/L |
| Total hardness: | 300 mg/L as CaCO₃ |
| Total alkalinity: | 198 mg/L as CaCO₃ |
| Temp (fall/winter): | 46-71° F (avg.=59° F) |
| Temp (spring/sum): | 61-89° F (avg.=59° F |
| Distribution Network: (Monitored Tank Y) ||
| Cl₂ dose at sampling pt: | 0.70 mg/L |
| TTHM lev. in network: | 20-72 µg/L |
| Average residence/age: | 72 hours monitored tank |
FIG. 4E
FIG. 4F

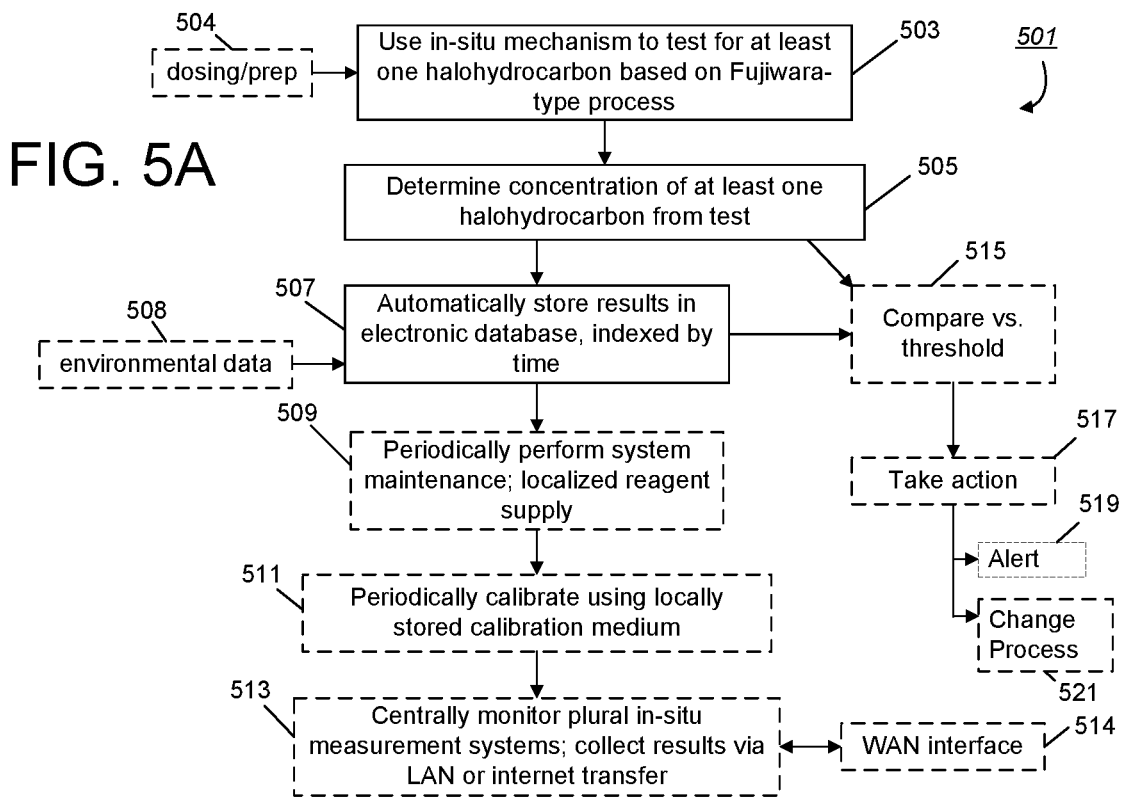
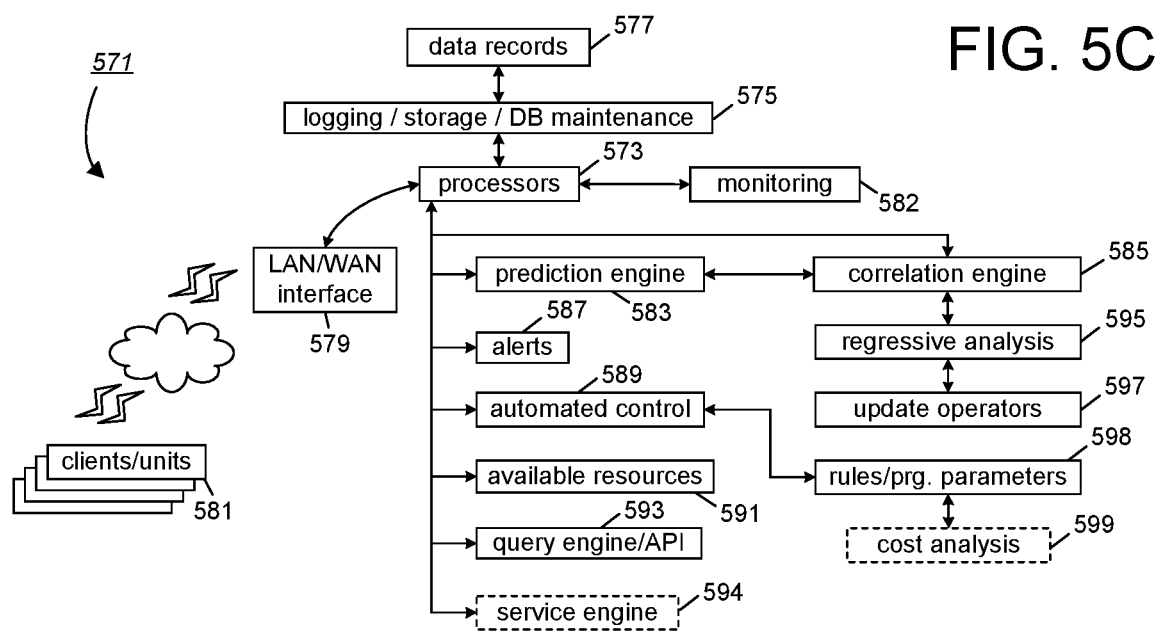

FORECASTING OF DISINFECTION BYPRODUCTS

This application claims the benefit of U.S. Provisional Patent Application No. 62/304929, filed on Mar. 7, 2016 on behalf of first-named inventor Michael J. West for "Forecasting of Disinfection By-Products." This application hereby incorporates that provisional patent application by reference, and further, also incorporates by reference U.S. Pat. No. 9,134,290 for "Methods and Apparatuses for Determination of Halohydrocarbons" and U.S. Pat. No. 9,222,921 for "Method and Apparatus for Determination of Haloacetic Acid (HAA) Presence in Aqueous Solution."

The present invention relates to forecasting of disinfection by-products (DBPs) levels in aqueous solutions. More particularly, this disclosure provides methods, systems, apparatuses and devices that can be used for forecasting DBPs levels expected to develop from disinfected water at a future point in time and for predicting DBP levels at desired locations and/or times in a water distribution system.

BACKGROUND

Water providers and distribution systems ("water supplies") typically treat water to ensure its safe use by humans or in the environment. In the case of potable water supplies, including without limitation municipal water companies, water is typically processed to remove unwanted particulate (including unwanted organics) and is typically disinfected by the addition of halogenating agents (halo is a prefix for chlorine, bromine and iodine). While these agents are beneficial to killing illness bearing microorganisms, they unfortunately can also produce various unwanted disinfection by-products (DBPs) that can be harmful to human health. These DBPs include halogenated DBPs such as trihalomethanes (THMs), haloacetic acids (HAAs), haloaldehydes, haloacetones, haloacetonitriles and chloral hydrate. THMs, in particular, head the USA EPA list of toxic and carcinogenic compounds highly regulated in drinking water. THMs as a group include chloroform ($CHCl_3$), bromodichloromethane ($CHBrCl_2$), dibromochloromethane ($CHBr_2Cl$) and bromoform ($CHBr_3$). These 4 THMs are included among the 25 volatile organic compounds regulated under the Safe Drinking Water Act (SDWA) of 1974, and are the most abundant, and chemically stable and persistent once formed. The formation and build-up of these DBPs occurs over time as a function of many factors, including organics present in the water, amount of halogenating agents added, pH, temperature of the water over time, residual sanitizers present, and age since the time of adding disinfectants. Other characteristics of the water supply system (including, without limitation, of the pipes and tanks used to transport and/or store the water, in-network blending with other treated water sources, disinfection re-dosing, and DBP mitigation strategies such as tank-aeration) can also influence the formation and decay of DBPs. Note that these factors can change over time and can strongly influence both the manner in which water is treated as well as which sources of water are relied on.

Water supplies therefore typically closely monitor DBP formation in potable water, either directly at a water treatment plant (WTP) or at remote locations in a water distribution network (e.g., close to the needed compliance points, such as near consumer taps). Both approaches have significant limitations. Early monitoring, for example at the point of water egress from a WTP, gives water treatment operators the opportunity to immediately control water treatment activities in response to DBP levels, but these DBP levels are typically low because the age of the water is so young; the detected levels can therefore be unreliable for predicting ultimate DBP levels in the network and/or at compliance points after the water has aged in the distribution network. By contrast, monitoring of DBP levels close to the compliance points provides much greater measurement accuracy of ultimate DBP levels, but the data is often too late to impact water treatment operations; this monitored water was produced several days earlier, and it can be difficult to change the current DBP levels. Moreover, the raw water characteristics, environmental factors (such as temperature) and/or treatment processes being employed may have changed significantly since the tested water left the WTP, and the measurement data might have little context to the current treatment of water at the WTP. Summarizing, traditional methods of monitoring of DBPs in disinfected water at an early water age can be unreliable for predicting future DBP levels of the same water later on in the water distribution process, and compliance point monitoring is typically too late in the process to yield to provide pertinent information as to how raw water should currently be treated.

FIG. 1 is used to graphically illustrate some of the dilemmas faced by water suppliers. As generally referenced by numeral 101, water in this example is assumed to be drawn from two sources, including a reservoir 103 and a well water supply 105. As is typically the case, composition of the water from the reservoir 103 can vary dependent on many factors, including how full the supply is, season, temperature, precipitation, current and past water demand and other factors; this water may require different treatments depending on these factors, e.g., to remove unwanted organics, metals and other particulate, and for disinfection. Water from the well water supply 105 is typically cleaner but typically is more expensive to extract, and not necessarily a resource that is quickly replenished. In this example, the water from the reservoir 103 is seen to be processed by chlorine dioxide injection 109 for disinfection, and by various processes, including coagulation and flocculation 111, sedimentation 113 and sand filtration 115, to remove unwanted dissolved components (including organics) and particulates. This filtered water can be combined with well water 105 at point 117; from there, it is subjected to ozone ($O_3$) treatment 119 and granular activated carbon (GAC) filtration 121, and to additional chlorination for final disinfection 123 before being sent out for distribution 107. Treated water as it is available may be added to stored, previously treated water in tanks 125, from which the distribution occurs. Sometimes, the amount of organics or other particulate present in the surface water (e.g. river) is especially heavy; under these conditions, the raw water can be supplied from the alternative source, as exemplified by the reservoir 103, and is to be subjected to different treatment activities including ultra-filtration 127 and reverse osmosis 129 for the removal of DBP precursor components in the water. As reverse osmosis can also remove certain desired minerals, this water can be re-mineralized 131 before being combined with water potentially drawn from other sources at junction 133. In such a system, DBPs are typically produced as a function of the composition of water from each supply 103/105, treatment processes applied, residual disinfectants present, and potentially other factors. In the case of FIG. 1, for example, the depicted water supply might choose to draw water from either the depicted reservoir 103 or well water supply 105 dependent on the costs of processing each, as well the tendency of each to produce DBPs later on in distribution. Note that there exist many possible sources of water not represented in the example of FIG. 1, including without limitation, river, aqueduct and desalinization sources, as well as water purchased from other water distribution systems. The two particular water sources seen in FIG. 1 are cited for purposes of discussion only. Generally speaking, ability to predict the tendency of water from each supply independently or blended in water treatment operations to form DBPs after treatment is considered valuable, as it can affect both how a water supply treats water from any given source (including how the water is treated chemically, and how many filtration and/or other treatments are used), as well as which source is used to provide water at any point in time. For example, in connection with the example provided by FIG. 1, an understanding of tendency of water at different points in the water supply network to produce DBPs (e.g., such as water from either of depicted water sources 103 and 105, or at any other point in distribution, such as at the exit of the depicted sedimentation process 113) can influence how the water supply treats water as well as the extent to which the water supply should rely on source 103 versus source 105. Naturally, real-world examples exist that are more complicated than the example represented in FIG. 1.

There exist two general classes of indirect experimental methods to predict the potential for a water sample to form DBPs. These processes typically attempt to measure one of the DBP precursors, specifically the quantity and characteristics of the organic matter in water, prior to treatment with halogenating agents, and to predict DBP formation potential dependent on the detected level of organics. One optical, non-destructive, class of processes typically operates by exposing a water sample to one or more specific wavelengths of light and detecting absorption of certain wavelengths of that light (e.g., UV absorption), while a second class of processes typically operates by attempting to convert organics to a specific compound or class of compounds (e.g., by heating or chemical conversion with an oxidant to carbon dioxide), and to then chemically or otherwise detect amount of that specific compound or class of compounds present. Generally speaking, these processes are not always accurate predictors of the capacity of a water sample to produce DBPs and/or may require a laboratory, time and expense.

There also exist techniques for directly measuring DBPs which have already formed and are currently present in the water. Elaborating, typical techniques for the measurement of DBPs, especially THMs, are based upon gas chromatography (GC) techniques and the use of an electron capture detector (ECD) or a mass-spectrometer (MS), although the analysis of THMs is not limited to these two most common techniques. In these methods, water samples are typically collected in vials, dechlorinated to prevent further reaction with chlorine, and brought to an offsite laboratory to analyze by GC-ECD or GC-MS. Total THM present (TTHM) can then be determined. These processes tend to be both laborious and time consuming, e.g., it can sometimes take as much as ten (10) days to get the lab results. Also, measurements may not accurately represent either (a) the water constituency at a different point in time or at a different location in the water supply or distribution network or (b) DBPs that develop after measurement. For example, as noted above, the constituency of water in a typical water supply changes can change significantly over minutes or hours, and thus a water sample collected at one time may not represent characteristics of water being delivered at a later time, even if the laboratory analysis for the sample is otherwise accurate. Furthermore, as noted, DBPs continuously form while residual quantities of chlorine and organic matter remain in the water, leading to progressively increasing concentrations DBPs, according to many variables associated with a specific water delivery system (such levels typically only decrease through evaporation from the water surface into with air); thus, a measurement at one time may not accurately reflect DBPs that form and decay after the sample collection and/or sample testing processes, e.g., based on organics present in the measured water which have not yet formed DBPs, or based on differential treatment of the samples (e.g., based on storage methods, testing methods and other factors). Given the health issues involved, it is generally desired to be able to accurately quantify DBP presence, especially the increasing levels of THMs, at all points in the water delivery process, especially at later points in time in the water delivery process (i.e., the so-called "formation potential").

What is needed are better techniques to measure DBPs on demand, and to estimate their elevated formation at future points in time (or at other locations) in a water distribution system, particularly at the remote points important for regulatory compliance, in a manner that does not rely on the existing methods. Ideally, such techniques could be employed in-situ at a water supply using fully automated equipment, or otherwise integrated into a self-contained appliance that could be installed at desired (potentially arbitrary) points in the water distribution path. Further still, a need exists for techniques that provide real-time or near-real-time measurement data to water supplies that permit those supplies to evaluate formation potential at future points in time and to manage various water treatment and/or sourcing options on a proactive, real-time basis, and that is robust to continuously changing water supply variables. The present invention solves these needs and provides further related advantages.

BRIEF DESCRIPTION OF THE DRAWINGS

FIG. 4C is a graph 451 that shows how the formation potential of THMs might vary rapidly in just hours for a typical water supply; the vertical axis of this FIG. represents THM concentrations in a range of 70+ micrograms per Liter of water, with each horizontal grid line representing an increment of 10 micrograms, while the horizontal axis represents time and each vertical grid line represents an increment of a day. The points connected by the solid line represent accelerated THM-FP levels. The plotted, dashed line corresponds to prediction of TTHM levels at some future time/location in a water distribution system, based on the recent real-time THM-FP measurements and the application of a function to characterize the water flow through the networks pipes and tanks.

FIG. 4D is a flow chart illustrating variables and actions associated predicting DBPs.

FIG. 4E shows example water quality data (after a treatment process).

FIG. 4F is a table illustrating environmental variables and measurement parameters that can be programmed, learned and/or tracked.

FIG. 5A provides a block diagram of an embodiment 501 that uses an in-situ detection mechanism to monitor DBP presence, specifically, using measurement techniques specific to THM measurement. As represented by dashed lines, the embodiment may optionally feature in-situ self-maintenance and self-calibration for maintaining accuracy and reliability using local storage for reagents, fluids, calibrations standards and other materials used in operation of the system; additionally, the in-situ mechanism may be part of or connected to a remote monitoring system or network that monitors several such mechanisms.

FIG. 5C provides a block diagram of an embodiment 571 relating to remote DBP monitoring using one or more servers, computers or other digital devices.

Figure 1:
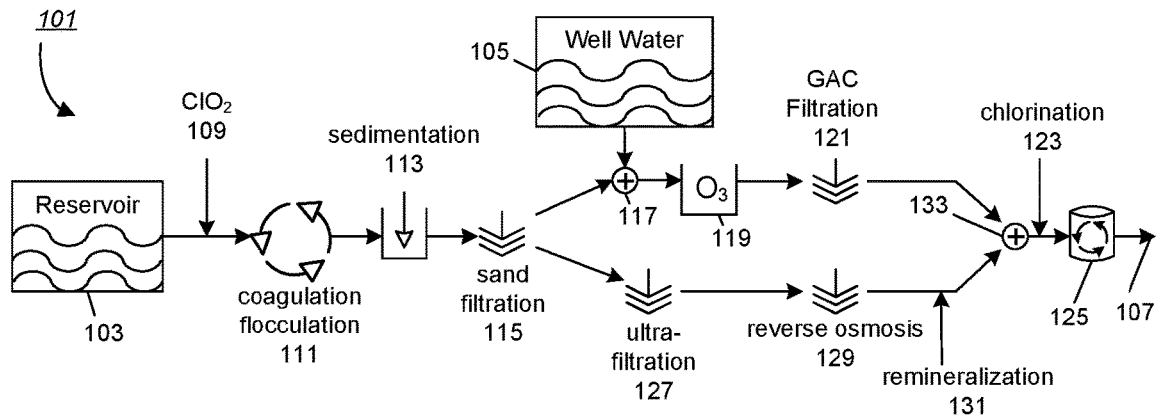
FIG. 1 illustrates an example of the activities and flow in an advanced treatment plant for potable water.

The subject matter defined by the enumerated claims may be better understood by referring to the following detailed description, which should be read in conjunction with the accompanying drawings. This description of one or more particular embodiments, set out below to enable one to build and use various implementations of the technology set forth by the claims, is not intended to limit the enumerated claims, but to exemplify their application. Without limiting the foregoing, this disclosure provides several different examples of techniques for in-situ measurement of disinfection by-products or "DBPs," and for related locally-based or network-based control of and monitoring of DBPs and their formation potential. Such techniques can be embodied, without limitation, as a water quality monitoring device (e.g., an in-situ DBP detection mechanism or a "monitor"), software and/or a control system for such a device (e.g., instructions stored on non-transitory machine-readable media), one or more network-based machines (e.g., one or more servers or other digital devices), methods for measuring DBPs and/or their formation potential, and methods for artificially aging collected samples to predict DBP formation potential. Although specific examples are presented in the context of potable water and DBPs, it is possible to apply these novel techniques to other applications as well (e.g., quality monitoring of non-potable water or of other substances). In the examples that follow, a primary application will be presented to the monitoring of THMs as the DBP of interest; it should be understood that the term DBP, however, is not so limited, and can extend to any disinfection by product, including HAAs and other substances. Thus, the principles described herein may also be applied to other methods, devices, systems and applications as well.

DETAILED DESCRIPTION

Techniques are presented herein for fast measurement of DBP formation potential and/or prediction of expected DBP levels at selected points in a water delivery network, based on (a) correlation of DBP measurement with environmental or other factors and/or (b) a measurement process that accelerates aging of water samples to advance DBP production in a manner correlated with a selective age and/or (c) predicting distribution network DBP levels from the DBP and/or DBP-formation potential measurements (by incorporating modeling of the blending of water of different treatment ages that occurs as it flows through the pipes and tanks, and other network operations). In one embodiment, these techniques can be partially embodied in an in-situ DBP detection mechanism or "monitor" which can detect trace levels of DBP and measure concentrations in real-time or near real time (i.e., less than two hours). In another embodiment, some or all of these techniques can be embodied in systems, devices, methods or software that form part of a water quality monitoring network, e.g., which can perform the correlation, measurement and/or prediction functions just referenced; in one embodiment, control of water supply selection and or treatment can be automated and made reactive to such correlation, measurement and/or prediction. In one implementation, these techniques can be rooted in near real-time measurement of THM presence, including total THM (TTHM) and THM speciation. Optionally also, the various described correlation, measurement and prediction techniques can be mixed in any desired combination or permutation, providing a powerful tool for estimating DBP formation potential from any water source or combination of water sources, in a manner which accounts for water supply parameters such as source commingling, accumulated water storage, weather, temperature and other factors, as desired. As should be appreciated, these techniques provide powerful tools that permit water producers and water distribution systems ("water supplies") to both regulate water source and treatment selection so as to ensure healthy water composition, while at the same time minimizing cost and maximizing efficiency associated with the water delivery process.

In one embodiment, by performing specific chemical and physical processes (including, but not limited to, heating the samples, and/or increasing the concentration of the chlorine-based disinfectant or other reagents), aging of a water can be artificially accelerated in connection with the measurement process, to facilitate and/or accelerate DBP formation; these DBPs are then measured in-situ, and detected levels of DBPs are then used to form the basis of accurate prediction of DBP concentrations potential, even though those DBPs may not have yet formed in the water supply which sourced the sample that was rapidly artificially aged. Optionally also, a system can correlate these measurements with other environmental or other data to more accurately predict DBP formation at any desired point in the water delivery network (e.g., later in time or at a specific location); for example, predicted DBP concentrations can depend on factors such as temperature and season. Thus, a measurement system and/or water monitoring network can take environmental and other factors into account in predicting what DBPs will be formed given source water characteristics (and which treatment processes should be used) to optimize water distribution. Many such factors may be optionally taken into account, including without limitation, characteristics of water available from respective water sources, changing characteristics of water injected into the system at various points in time, temperature, water age, tank or pipe materials, time of day, week or year (e.g., season), treatment processes available and the extent of their application, and/or other factors.

In another embodiment, techniques are presented for locally-based or network-based prediction of DBP presence at a desired point in a water delivery network based on in-situ DBP measurement processes (e.g., based on artificially aged samples or otherwise) and correlation of measurement results with data from one or more sources of other data. Once again, correlation can be based on many factors such as temperature, season, pH, residual sanitizers present and any further network re-dosing to maintain stable residual disinfectant levels, characteristics of water available from respective water sources, changing characteristics of water injected into the system at various points in time, water age, in-network blending at interconnects with other supply systems, tank or pipe materials, time of day, week or year, treatment processes applied (both at the original plant and otherwise in the network), and/or other factors. These techniques can be optionally embodied in software, in a device or monitor, or in a related network or computer system, or method of operating such things. Optionally, operational or computational parameters of the DBP forecasting methods can be improved or learned over time, to provide for better results.

Note that the techniques described herein can be applied to a wide variety of analytical techniques. For example, instead of testing treated water, the described techniques can be applied to raw water, for example, so that operational decisions can be made early. To this effect, raw water can be dosed, treated or processed in any desired manner (e.g., by adding disinfectants, chemicals, reagents, boosting elements, or in another manner) and then tested/measured in the manner otherwise described. As an example, if a water utility has the opportunity to acquire water from two or more sources (e.g. rivers with quick changes in their composition due to weather events, lakes, aquifers and water imported from aqueduct supplies), it can apply nominal dosing/buffering/pH adjustment/cooling/heating/mixing and/or other processes to both samples for purposes of comparative or other analysis. The same processes can also be performed for already treated samples, e.g., additional doses, buffers, pH adjustment, cooling, heating, mixing and/or other processes can be performed on such samples prior to measurement, and used to make an inform decision pertinent to the use and/or processing of water from an associated water supply. Again, the ability to quickly measure DBP levels and/or measure DBP formation potential on an accelerated basis facilitates early decisions as to source selection and treatment processes.

This disclosure will be generally organized as follows. First, the operation of an in-situ DBP detection mechanism will be introduced, with reference to FIG. 2. Second, an exemplary water quality monitoring network will be described, relative to FIG. 3A, with breakout examples provided showing how such a network can be applied to forecast DBP levels at any temporal or physical location in a water distribution system (FIG. 3B) or to measure DBP formation potential of specific sources at specific points in time. Third, the optional use of an accelerated aging process during or in connection of measurement will then be discussed, together with data or factors that can be correlated with such measurement and used to improve DBP predictions (FIGS. 4A-4F). Subsequently, a more detailed embodiment or a remote monitoring network will be presented (i.e., relative to FIGS. 5A-5C). FIGS. 6A-6C will be used to discuss one example of software and/or database design that can be used in association with the remote monitoring network or other systems described herein. Finally, FIG. 7 will be used to discuss correlation of water aging with parameters of the accelerated aging process, such that mapping information can be developed to permit accurate formation potential measurement for a sample for DBPs at a selective, future time, based on heating/processing characteristics adapted to simulate the selective water age at-issue.

Prior to proceeding to the additional discussion, it would be helpful to first introduce certain terms used herein.

Note that as used herein, "circuitry" can refer to analog or digital electronic elements (e.g., dedicated logic gates), either arranged as special purpose circuitry that necessarily performs a certain function when electrically motivated, or as general purpose circuitry (e.g., a processor, FPGA or other configurable circuit) that is controlled or otherwise configured by instructions (software) so as to adapt that circuitry to perform a specific function and cause that circuitry to operate as though it was special purpose circuitry. In the case of software or other instructional logic, the instructions are typically written or designed in a manner that has certain structure (architectural features) such that, when those instructions are ultimately executed, they cause the one or more general purpose circuits or hardware devices to necessarily perform certain described tasks. "Logic" can refer to software logic (i.e., instructional logic) or hardware logic (e.g., a digital chip or board design) or a combination of these things. "Non-transitory machine-readable media" means any tangible (i.e., physical) storage medium, irrespective of how data on that medium is stored, including without limitation, random access memory, hard disk memory, optical memory, a floppy disk, CD, server storage, volatile memory, nonvolatile memory, a memory card, a storage drive and/or other tangible mechanisms where instructions may subsequently be retrieved by a machine. The machine-readable media can be in standalone form (e.g., a program disk, solid state memory card, whether bootable or executable or otherwise, or in other memory) or embodied as part of a larger mechanism, for example, resident in a laptop computer, portable or mobile device, server, data center, "blade" device, subsystem, electronics "card," storage device, network, or other set of one or more other forms of devices. The instructions can be implemented in different formats, for example, as metadata that when called is effective to invoke a certain action, as Java code or scripting, as code written in a specific programming language (e.g., as C++ code), as a processor-specific instruction set, or in some other form; the instructions can also be executed by the same processor or common circuits, or by different processors or circuits, depending on embodiment. For example, "instructions stored on non-transitory machine-readable media" typically refers to software stored on disk or in other physical memory or storage, where the software is structured such that when it is later (ultimately) installed or executed by an operator or end user, it configures a machine (e.g., one or more processors) so that they operate in a prescribed manner. In one implementation, instructions on non-transitory machine-readable media can be executed by a single computer or processor and, in other cases as stated, can be stored and/or executed on a distributed basis, e.g., using one or more servers, web clients, or application-specific devices, whether collocated or remote from each other. Each function mentioned in the disclosure or FIGS. can be implemented as part of a combined program or as a standalone software module (i.e., an invocable or callable program or subroutine), either stored together on a single media expression (e.g., single floppy disk) or on multiple, separate storage devices, or in the form of dedicated circuitry or circuitry combined with such software. Throughout this disclosure, various processes will be described, any of which can generally be implemented as instructional logic (e.g., as instructions stored on non-transitory machine-readable media), as hardware logic, or as a combination of these things, depending on embodiment or specific design. "Module" as used herein refers to a structure dedicated to a specific function; for example, a "first module" to perform a first specific function and a "second module" to perform a second specific function, when used in the context of instructions (e.g., computer code) refers to mutually-exclusive code sets. When used in the context of mechanical or electromechanical structures (e.g., an "measurement module," it refers to a dedicated set of components which might include hardware and/or software); for example, a "measurement module" and a "formation potential calculation module" would refer to dedicated, mutually exclusive structural elements for performing these functions. In all cases, the term "module" is used to refer to a specific structure for performing a function or operation that would be understood by one of ordinary skill in the art to which the subject matter pertains as a conventional structure used in the specific art (e.g., a software module or hardware module), and not as a generic placeholder or "means" for "any structure whatsoever" (e.g., "a team of oxen") for performing a recited function. As also generally used herein, a "mechanism" or "device" refers to a unit of hardware comprising one or more mechanically-, electrically-, fluidically- or electromechanically-actuated elements.

As used herein, a water quality monitoring network refers to a set of one or more systems or devices that receive measurements of water characteristics (and optionally control the measurement process), from one or more sources or measurement points. A water distribution network, by contrast, refers to paths, processes, blending, treatments and other handling of water from a water source until delivery of the water to a client; for example, it can include a system managed by a municipal water company, and it can also refer to a collections of entities/routes/systems extending from water collection to delivery to an end consumer (e.g., at a tap).

Finally, note that many of the embodiments presented below will focus on THMs as being one type of DBP that is particularly difficult to safely measure in-situ; however, it should be understood that many of the principles described herein can also be applied or adapted to the measurement of other DBPs (e.g., HAAs and other types of DBPs), particularly to the forecasting or measurement of formation potential for such DBPs, without departing from the inventive principles taught herein; in such cases, the use of other chemical procedures can be substituted and used to adapt the measurement process in a manner suitable to measurement of the particular DBP at-issue.

Figure 2:
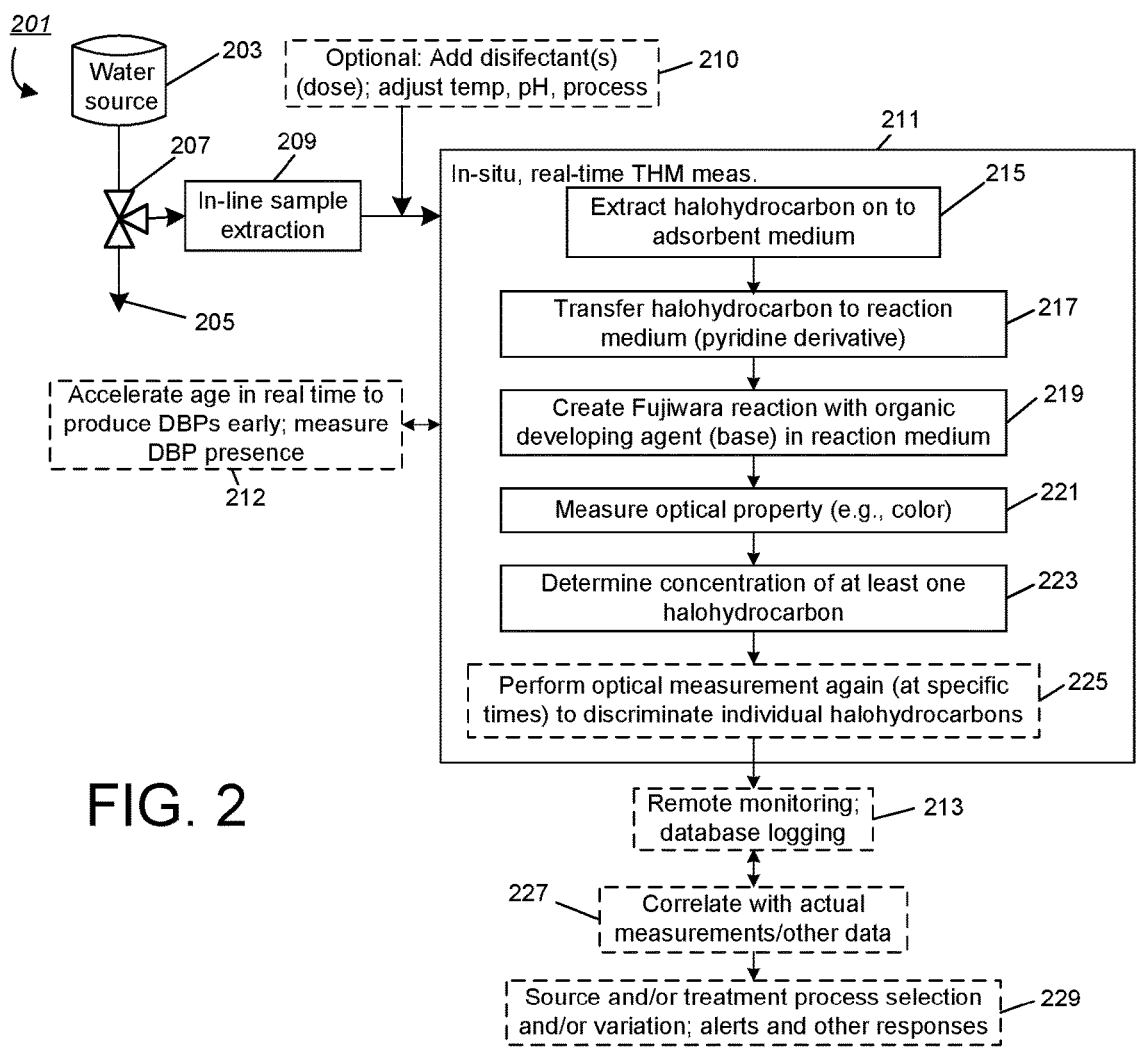
FIG. 2 a block diagram of an embodiment 201 that uses an in-situ detection mechanism to monitor DBP presence, specifically, THMs. As denoted by dashed-line blocks, the embodiment may optionally feature (a) rapid age-acceleration processes for disinfected water samples and subsequent determination of their DBP levels, (b) remote monitoring and associated database storage of logged measurements, (c) correlation of measurement results with other (internal or external) data, in order to predict DBP formation at certain temporal or physical points in the water distribution process, and (d) reactionary mechanisms based on such prediction including without limitation, water source variation/selection, treatment variation/selection, the generation of alerts, and/or other responses.

FIG. 2 provides a block diagram of an embodiment 201 of an in-situ DBP detection mechanism. More specifically, FIG. 2 shows a method and system for measuring THMs in samples which are automatically drawn from a water source 203; the measurement process is based on a modified Fujiwara reaction, for example, as described in detail in U.S. Pat. No. 9,134,290, and can be performed in real-time or near-real time (e.g., with results generally available within thirty minutes of measurement). Numeral 211 refers generally to this steps used to measure the current level of THMs formed in the drawn sample and/or the formation potential for such THMs. In this latter regard, the depicted system selectively uses a process to artificially age the water sample 212 to accelerate further THM production based on the composition and quantities of remaining residual precursors that continue to form yet more DBPs in the water (including organics the residual organics and bromide still present in the sample, and the current level of chlorine). As will be shown below, this aging process can be performed by heating the water sample to a controlled temperature for a controlled amount of time, where both the temperature and time have been correlated in advance with a particular age representing the forecast period for the sample measurement (e.g., the aging process corresponds to a "selective" age, and the process can be altered to simulate other ages). For example, if it is desired to measure THM presence that can be expected to exist after three days of aging the water at eighty-five degrees Fahrenheit, the amount of heating and the duration of heating applied (generally 50-70° C. for 30-60 mins) is selected dependent on these metrics and optionally the current water temperature. As noted earlier, other processing can also be performed, for example, raw source water (or previously processed but chlorine depleted water,) can be dosed (re-dosed) with chlorine, optionally pH adjusted with buffers, or temperature controlled, all per numeral 210; other types of processing can also be performed. As these examples demonstrate, other environmental factors such as water source temperature, season and other considerations may optionally be factored into selection of the specific heating profile, desired time of heating, and the extent of chlorine processing (if necessary). The result of the accelerated aging process is a water sample with advanced DBP formation and/or decay. This sample is then measured using the various steps 211 represented in FIG. 2, to detect DBPs then existing in the artificially aged sample. Per numeral 213, results of measurement can be logged either locally or in a remote database. As indicated by block 213, in one embodiment, this logging (and related monitoring) can be performed remotely; for example, as discussed below, a network can remotely control an in-situ DBP detection mechanism to automatically draw samples and perform ad hoc readings, operational tests and calibrations, as well as to program various parameters related to measurement factors (e.g., age to be simulated by the heating process and so forth). Advantageously such a network or a control system automatically receives readings (measurements) via a local area network ("LAN") or wide area network ("WAN") connection, where those readings are based on DBP measurements processed in real-time or near-real time from each DBP measurement system, as they are completed, in a defined messaging format; the readings can be accompanied by data from other systems (for example, representing pH, water temperature, and other water quality statistics). Note that in one embodiment, the in-situ DBP detection mechanism can simulate aging of a water sample for a selective age, or 2) can be commanded to measure only the current DBP concentrations (without application of the accelerated aging steps); as an example, a THM detector is advantageously of an architecture that permits it to be selectively commanded to measure current THM levels (e.g., TTHM and/or specific species concentrations) or to measure the higher THM formation potential employing the set of operational parameters (heat/time/chlorine dosing) most likely to provide a good correlation with THM levels that would in fact be produced at a specifically selected (or understood) future age.

As noted earlier, it is generally difficult to measure THMs without use of offsite laboratory analysis. The system represented by FIG. 2 performs this measurement in-situ, not just for total THM ("TTHM") but optionally also for individual THM species as well; all results may be logged. As indicated by numeral 205 in FIG. 2, it is assumed that water from water source 203 is to be provided to a destination (e.g., a water delivery customer) and that, at some point along this path, an electronically-actuated valve 207 or other actuation mechanism is used to draw a sample of water, for example, 100 mL. Subject to any desired dosing or other processing, 210 automated processing is then performed on this sample 209 in order to identify THMs either present in the sample currently or that might be formed in the future. Following any desired sample aging process, the sample is processed to extract at least one halohydrocarbon (THM) to an adsorbent medium, as indicated by step 215. After being concentrated on the adsorbent medium, the halohydrocarbons are transferred to a reaction medium having a pyridine derivative, as referenced by numeral 217. In addition to the pyridine derivative, the reaction medium may be an organic solution used to elute the analytes from the adsorbent medium (such as acetonitrile). Alternatively, the analytes may be removed by a thermal desorption process, such as by heating the adsorbent medium to a point where the analytes become volatile, and then sweeping the volatile analytes into the reaction medium using gasses such as nitrogen or air. The reaction medium is typically of a known volume, such that DPB presence will be represented as a per-unit volume concentration. As depicted by reference numeral 219, the analytes are subjected to a modified Fujiwara reaction, based on an organic developing agent (such as the hydroxide of an organic cation) and an optional organic co-solvent, at a controlled, elevated temperature, again, as more fully discussed in U.S. Pat. No. 9,134,290. As the reaction proceeds, the color intensity of the reaction medium changes; this optical property is measured during the reaction, per numeral 221. Based on the measured optical results, the halohydrocarbon concentration is determined, as indicated by reference numeral 223.

In fact, there may be several halohydrocarbons (e.g., THMs) present in unknown quantities, and the system of FIG. 2 may therefore optionally be applied to discriminate between the THM species and to determine their individual concentrations. As indicated by dashed-line (i.e., optional) process block 225, the optical properties of the reaction medium may be measured two or more times, at different times, to detect the change in color intensity. As described with respect to FIG. 4 of U.S. Pat. No. 9,134,290, based upon predetermined data, total THM presence may be determined and individual THM species concentrations determined from this data based on real-time or near real-time measurements. In addition, per numeral 227, in one embodiment, measurements can be correlated with other data and used to adjust, learn or improve the heating/aging parameters supplied to the system or a prediction algorithm for formation potential or DBP level prediction based on many variables (e.g., including one based on in-situ THM measurement or measured formation potential); as an example, if the system is configured to provide predictions of THM levels at a specific water retention age and location (e.g., seventy-two hours later at the exit of a designated storage tank), assuming stable operation of the network distribution system, the early measurement data associated with the "artificially and rapidly aged" samples can be compared with the later measurements taken from the tank-exit water supply, which has been slowly and naturally aging in the distribution system, and so forth. With a sufficiently large quantity of comparative data (predictive THM data from earlier THM-FP sample analyses and actual THM levels determined in samples collected from the forward projected dates/location) analysis of the correlation using regressive analysis can be used to adjust/improve any of the process variables employed that affect the degree of THM-FP rate acceleration (e.g. adjustment to the water-heating time and/or temperature). The system's software can automatically adjust prediction through programmed response to known natural changes (e.g. seasonal dates), or sensed changes (e.g. self-and-internal measurements of the original water, or the same information inputted through an interface from another temperature recording device). Furthermore, the system can maintain a set of best operation parameters that correspond to a set of previously-learned water-treatment or network control configurations, and then selected as a 'recipe' by a water treatment operator with knowledge of these operational change that affect the natural aging of the sample—particularly those future events or activities that occur in the network, after the sampling and/or DBP prediction and/or formation potential prediction. Per numeral 229, predictions can also be used to take automated actions, including without limitation, generating alerts, emails, voice mails or other messages for automated sending to human operators (either locally or at a remote water supply), automatically controlling water source selection and/or adjusting flow rates, and/or modifying applied water treatments; other responses can be taken as well. Returning briefly to the example provided by FIG. 1, based on in-situ measured formation potential or predicted DBP levels at a point downstream in the water delivery network, the depicted water supply network can be prompted to invoke an additional filtration path 115/127/129/131 on an automated basis, or to reduce reliance on reservoir 103 in favor of the well water supply 105, or to provide additional/less chlorination 123 or chlorine dioxide addition 109, or to increase/decrease sand filtration 115, and so forth. Note that the disclosed techniques can optionally be practiced within a closed network (e.g., within the network of a specific water treatment company or governmental entity) or on a service bureau basis (e.g., a services supplier can perform logging and provide alerts and automated control prompts to respective clients, as will be further described below in relation to FIGS. 6A-6C).

Figure 3A:
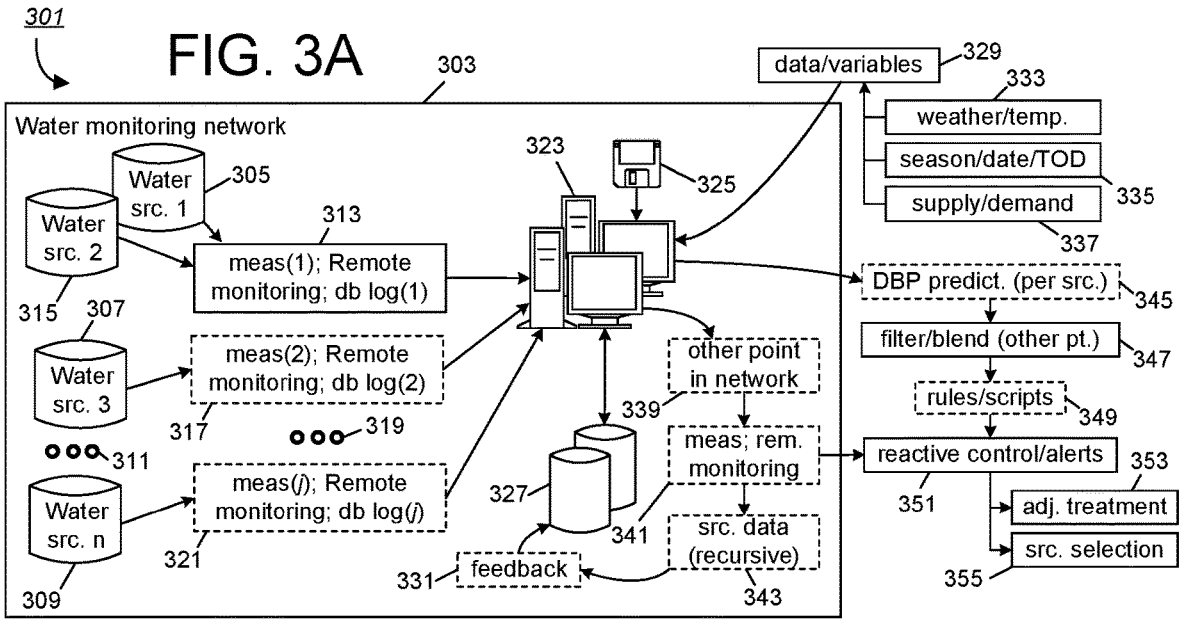
FIG. 3A shows a water monitoring network 303 that uses one or more in-situ DBP detection mechanisms ("monitor").
Figure 3B:
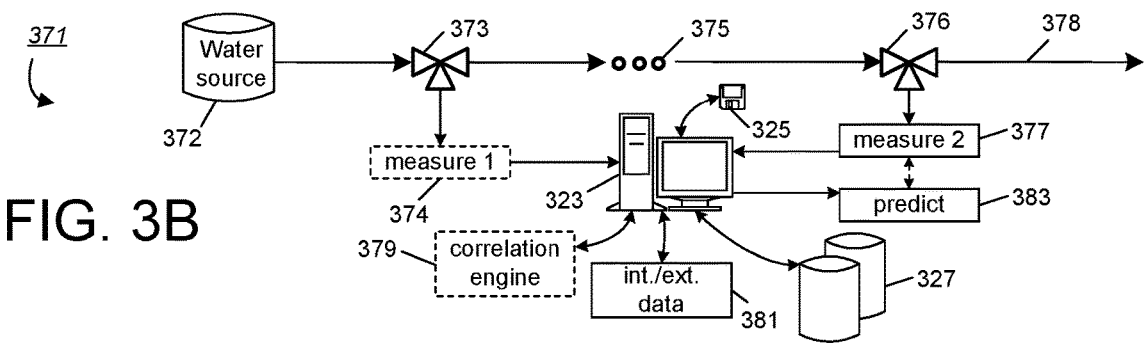
FIG. 3B is a block diagram showing one embodiment that predicts DBP levels at a desired temporal or physical point in a water distribution network based on correlation of DBP measurement with internal or external data.
Figure 3C:
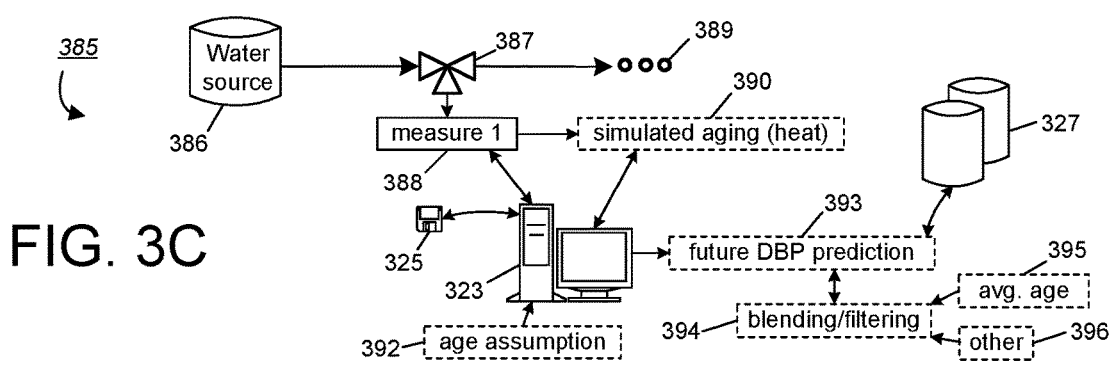
FIG. 3C is a block diagram of an embodiment that measures DBP formation potential for a sample based on techniques that rapidly accelerate sample aging to produce DBPs early and that then measures actual DBP quantities in the aged sample.

FIGS. 3A-3C illustrate several implementations relating to prediction of DBP levels.

Specifically, FIG. 3A provides an illustrative diagram 301 showing a water monitoring network 303 and various actions that can be taken by that water monitoring network. In the example of FIG. 3A, it is assumed that a water supply (e.g., a municipal water company) has a number of possible sources of water, including water source 305, water source 307, water source 309, water source 315, and potentially other sources as represented by ellipses 311. It is further assumed that the water supply utilizes in-situ DBP detection mechanisms 313, 317 and 321 as described herein; once again, these mechanisms are exemplified as measurement mechanisms for THM concentrations (e.g., TTHM), but analogous mechanisms can also be used for detection of other DBPs (including without limitation, HAAs; see, e.g., without limitation, U.S. Pat. No. 9,222,921). Other types of automated measurement systems can also be used, for example, pH detectors, water and ambient air temperature detectors, chlorine monitors (in all relevant forms of the chlorine chemical speciation), detectors for various types of metals, organics or other substances, and so forth. Note that while FIG. 3A shows multiple in-situ DBP detection mechanisms, a given water supply might have only one such mechanism (313, illustrated in solid lines), and additional mechanisms 317 and 321 are optional (represented by dashed-lines). Conversely, a given water supply could have many more than three DBP detection mechanisms, as again represented by ellipses 319. Depending on configuration, an in-situ detection mechanism can be configured to draw intermittent samples from a single water supply (e.g., as detection mechanism 321 draws samples from water source "n," 309) or from multiple alternate sources (e.g., as detection mechanism 313 draws water samples alternately from depicted water sources 305 and 315).

Each in-situ detection mechanism is further seen to be networked with one or more computers (e.g., servers) 323 acting under auspices of suitable software 325 (denoted by a floppy disk icon in the FIG.). In fact, FIG. 3A denotes several possible architectures including: (a) one where each in-situ detection mechanism has its own dedicated control system (e.g., which shared data with network servers 323); (b) one where measurement control and control over maintenance functions such as system renewal and calibration are cooperative; (c) one where computers 323 are part of a local infrastructure (and where, for example, the processors can represent embedded systems or FPGAs); and (d) one where control is entirely remote (e.g., computers 323 issue commands over a LAN or WAN to take specified actions and effectuate specifically-commanded sequences). Other configurations are also possible. For each architecture, as each in-situ detection mechanism performs a measurement and computes a result represented measured DBP presence, the in-situ detection mechanism reports the result to the computers 223, which then store the reported results in a database 327 for purposes of logging and for purposes of current and prospective prediction services.

As noted earlier, in one embodiment, the depicted water monitoring network 303 and computers/servers 323 provide predictions of DBP levels at a specific temporal or physical point based on correlation of measurement results with internal or external data or variables 329; for example, if a DBP concentration of "x" is measured by in-situ detection mechanism 313, and short-term atmospheric temperatures are expected to be warm, this can influence expected DBP concentration at a specific, later point in the water delivery process. Thus, the computers/servers 323 can produce a forecasted concentration that is different than "x" (e.g., greater than "x" based on the warm expected temperatures). Other factors, such as average water age at such a tank, can also be factored into the prediction; for example, if the current season is warm and dry, leading to an expectation that average water age at a tank is less, computers/servers 323 can lower DBP predictions (and command reduced sanitizer dosage) based on the assumption that water need not be sanitized for long term storage. As indicated by numerals 333, 335 and 337, variables such as current weather or temperature, season, date, time of day, storage tank level, accumulated precipitation, current supply and demand, and many other variables, can all optionally be factored into this analysis. This listing is non-limiting, e.g., as will be realized by one having ordinary skill in the art, many different variables may bear on DBP formation. As implied by FIG. 3A, the one or more computers/processors 303 advantageously build a model (algorithm) for prediction and update associated coefficients to predict DBP concentration at a given point and/time in the network given pertinent environmental variables and other factors; such a model can optionally be built and/or periodically updated using regression analysis.

Numeral 339 represents that, as just above, these predictive techniques and system architecture can be structured so as to permit forecast of DBP levels at any desired location or point in time. For example, it is possible to monitor water sources 305, 307, 309 and 315 for DBP presence and, based on the data/variables 329, to predict DBP levels in a particular storage tank in the network. The system can be designed to provide feedback 331 based on actual downstream measurements 341 in order to update coefficients and prediction parameters, for example, using a recursive analysis 343 that looks at past predictions and adjusts the coefficients/parameters in dependence on divergence of true data from those predictions.

Note that the measurements from each in-situ DBP detection mechanism can represent in this embodiment either current DBP levels or measurement of formation potential, with the difference being that the in-situ DBP detection mechanism can be commanded to accelerate aging of a drawn water sample according to established heat, temperature and/or other parameters, in order to advance DBP formation to a desired degree. Per numeral 345, formation potential can be computed for each source for a selective age, and given certain assumptions such as average temperature during aging; for example, in-situ detection mechanism 317 can be commanded to measure formation potential using an assumed age of three days henceforth and an assumption that the water being measured will experience an average temperature of X degrees. In such an example, in-situ detection mechanism 317 applies a heating profile (e.g., dependent on the three day period and the assumed X degrees) to artificially accelerate aging of a drawn water sample; it then measures the manipulated DBP levels currently in that age-accelerated water sample and provides measurements to computers/servers 323. Note that the measured formation potential may or may not inherently be an accurate predictor of DBP concentration at any specific point in time or in the water delivery network; rather, the formation potential represents a measurement of DBP level expectation based on water sample that represents the state of water in a water supply at a particular instant in time, given assumed variables relating to the aging process. Measured formation potentials respective to one or more water sources and one or more sample times are therefore advantageously blended, modified or combined, so as to develop a prediction of DBP concentration that models a particular time and/or point in the water distribution network 303. Taking a simplified example of this where water is drawn from a single water source and is then treated and accumulated (blended) prior to customer delivery, the water will typically present ever-changing characteristics (and therefore continuously-changing formation potential); the DBP concentration that will be present in the accumulated water (e.g., in a storage tank) will therefore be a combination of a time-weighted window of potentially many formation potential measurements. Therefore, in a model adapted to this simplified example, periodic (e.g., hourly) formation potential measurements from in-situ detection mechanism 317 can be convolved with or blended with formation potential measurements for time-wise adjacent samples from the same water source, using a time window selected in dependence on average age of water in the storage tank of interest; the greater the average water age, the greater the accumulation and blending of water having dissimilar characteristics (and the wider the window of the applied function need be). By contrast, when average age is low, there is less blending/aggregation, and the optional blending function 347 can process a narrower range of formation potential measurements to develop an accurate prediction of DBP concentration, on a weighted basis if desired. As denoted by numeral 349, in one embodiment, the desired blending and associated predictions can be based on rules or scripting (349), for example, as established by the specific water supply as pertinent to its unique characteristics and circumstances. Rules/scripting 349 can also be used to take actions 351 in response to measurements and/or predictions. For example, the rules/scripting 349 can be structured so that, if modeling forecasts elevated DBP concentrations (i.e., exceeding one or more thresholds), automated audible, email or voice mail alerts are triggered. That is, the one or more computers/servers can be caused to continuously (or periodically) build and evaluate predictions for DBP concentrations at select temporal or physical points in the water distribution network; when certain conditions are evaluated to be true, as defined by a pertinent script or rule, the pertinent script or rule causes the computers/servers 323 to automatically generate a response. The response can include operator notifications as well as automated machine commands. That is, per function blocks 353 and 355, it is possible to automatically generate and transmit machine control values that will adjust treatment of water from specific sources or at specific locations, or switch source reliance. For example, as was referenced above in connection with the discussion of FIG. 1, additional filtration can be selected if DBP formation potential is excessive, or alternatively, relative reliance on water sources and/or flow rates can be modified.

FIG. 3B shows an embodiment 371 directed to forecasting of DBP concentrations generally in such a system. That is, in such an embodiment, DBP measurements are correlated with other factors or variables and used to predict DBP concentration at a specific point/time in the water distribution network. A water source 372 is seen to supply water for downstream delivery 378. At point 373, a bleed valve, sample port or other sample extraction mechanism is used for in-line sample extraction, i.e., for provision to and measurement 374 by an in-situ DBP detection mechanism as referenced earlier. Measurements are reported to processor(s)/computer(s) 323, again acting under auspices of appropriate software 325. In this example, it is assumed that it is desired to forecast DBP levels 383 corresponding to a later point 376 in the water distribution network. As indicated by FIG. 3B, this type of process or prediction is advantageously calibrated using downstream measurement of actual DBP concentration 377, for example, using a second in-situ detection mechanism to perform automated sample measurement at the later point 376 being modeled; other techniques such as remote lab measurement can also be used for this correlation. These measurements 377 are compared to the predicted/forecast values 383, with results provided to a correlation engine 379 (e.g., implemented as part of software 325) to improve prediction/forecast accuracy. As noted, correlation can also be based on other variables, as represented by internal or external data 381, with predictions, measurements, coefficients and variables/parameter values being stored in database 327. If desired, the modeling represented by correlation can reflect comingling of water having difference characteristics (e.g., from different sources or based on accumulation, processes or materials), as represented by ellipses 375.

FIG. 3C shows an embodiment diagram 385 directed to formation potential measurement. Here, a water source 386 is similarly seen to supply water for delivery to downstream points 389 in the water delivery network. At point 387, a bleed valve or sample port, or other sample extraction mechanism is used "in-line" to draw small samples corresponding to water from the water source 386 at a particular point in time. As before, the sample is measured in near real-time (i.e., <2 hours) for DBP presence and concentration 388, for example, TTHM and THM species concentrations. However, as indicated by numeral 390, in this case, the in-situ detection mechanism further accelerates aging of the drawn water sample prior to measurement, e.g., according to a heat profile that has been established a priori. As noted earlier, generally, the applied aging process heats the sample to a temperature of 50-70° C. for thirty to sixty minutes, depending on the desired age simulation effect. These parameters represent certain age and temperature assumptions 392 that have been previously correlated to the amount of aging desired. The in-situ detection mechanism then detects DBP concentrations in the "accelerated" sample, and reports these measurements to computers/servers 323, for logging in the database 327. As indicated by numeral 393, the measured results can then be used in an algorithm or model for purposes of providing an automated prediction of DBP levels, i.e., will exist at a future point in time or particular downstream point in the water delivery network (e.g., at a particular water storage tank). For example, per numerals 394, 395 and 396 the measured formation potential or prediction can be blended in dependence on average age of accumulated water, or other factors, just as before.

Reflecting on some of the operations discussed with reference to FIGS. 3A-3C, a monitoring network can be predicated on in-situ measurement of DBP concentrations. These measurements can be used to predict DBP levels at a particular point in the water delivery chain, for example, at a specific time and/or location. In one embodiment, the in-situ detection mechanism applies a process to accelerate the effects of sample aging, such that DBP concentration measured in the sample represents an assumed (selective) later point in time.

FIGS. 4A-4E are used to discuss certain concepts relating to accelerate aging of samples.

Figure 4A:
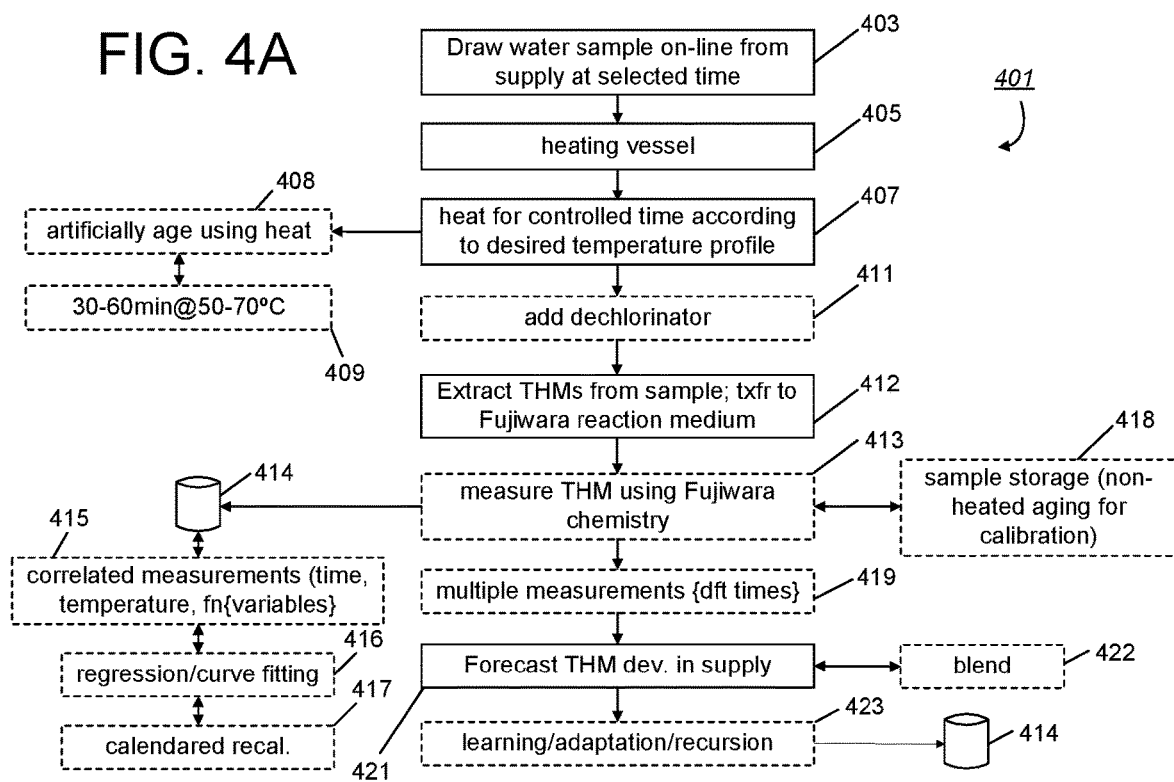
FIG. 4A provides a block diagram of an embodiment 401 of a method and system for measuring halohydrocarbons (THMs) using a modified Fujiwara reaction, including an option for accelerating the aging of a sample in order to measure DBP formation potential.

More specifically, FIG. 4A provides a block diagram 401 for an embodiment that performs DBP measurement based on accelerated sample aging. In this embodiment, a measurement system is once again employed locally to extract water samples in-line at a water supply (or distribution facility) on a remote, automated basis 403. Note that, once again, the samples can be raw water samples or already-treated samples; whatever the source, an in-situ mechanism receives or draws water, and then performs a series of steps to extract and concentrate DBPs. For example, if raw water is being measured, the water can be chlorine-dosed (and have other optional buffering performed, e.g., such as might occur in a WTP), and then is processed for DPB measurement based on desired (assumed) environmental factors. That is, as previously referenced, a water supply may add disinfection agents to water, including chlorine, bromine or other halogen-based compounds for purposes of sanitizing the water. Dependent on various factors including organics still present in the water (and the cost and nature of treatment processes selectively applied to filter the water), DBPs form as a by-product of such treatment; the longer water is exposed to these sanitizers given the water's constituency and environmental factors, the more DBPs will generally be formed (in a manner potentially varying by DBP specie). Note there may be a period of hours or days after water is disinfected before that water is delivered to a consumer, and if the water is stored or travels with a sanitizing agent after leaving a water processing facility, DBPs can be formed to varying degrees dependent on factors mentioned previously. The in-situ mechanism in this embodiment is used to forecast DBP formation potential at such a future point in time by accelerating aging of the sample and by then taking measurements of DBPs in the accelerated sample. The depicted embodiment is directed to forecast of THM formation potential. Specifically with respect to THMs, this accelerated aging can be performed by heating a water sample in a pre-treatment (heating) vessel 405 at one or more specific temperatures, and for associated durations 407, to accelerate THM formation. Note again that, as referenced in FIG. 4A, an example duration and heat level can be 30-60 minutes at a temperature of 50-70 degrees centigrade 409, with the specific heat/duration chosen so as to mimic a particular (e.g., selective) amount of aging; this is contrasted with a typical THM measurement process performed at ambient temperature (e.g., 20 degrees centigrade). Following any desired aging process, a dechlorinating agent 411 can then be added to the sample to quench all reactive chlorine and thus terminate the first step of DBP production (the incorporation of the reactive halogen onto the carbon atoms of the organic matter). THMs can at this time be extracted 412 by pre-concentration and extraction into a known volume of reagent, and the extracted THMs can immediately be measured (e.g., for total THM or any desired THM species). For example, the extracted THMs are optionally measured using modified Fujiwara chemistry as taught herein to measure individual an individual THM species concentration 413. Measurements thereby represent THM formation potential for the water supply that sourced the water sample at the particular point in time, and can be used to forecast expected contribution to DBP levels at a later point in the water delivery process. The measurements and/or forecasts can be stored in a database 414 along with ambient measurement factors such as time, temperature, pipe/tank materials and pipe/tank age, and values for potentially many other variables 415. Such data can also be subjected to regression analysis or other curve fitting 416 in order to generate and/or improve an equational dependency of forecasted DBP concentration relative to measured formation potential, actual DPB concentration at various at various water sources or supply points, and/or the other variables. Finally, the in-situ mechanism is optionally programmed to, on a calendared basis, automatically remeasure DBP concentrations (and/or formation potential), and to report measurement results on a calendared basis 417. As will be discussed below, measurement results and/or DBP predictions can be compared to thresholds and used to generate alerts/alarms if lesser than or greater than expected. Per numeral 418, unused water from drawn water samples can also be stored in a manner corresponding to age assumptions and measured at a later point in time (e.g., 3-7 days later) in order to calibrate the formation potential measurement and adjust factors based on feedback, to improve accuracy. Per numeral 419, multiple measurements can be taken at different points in time in order to derive THM speciation. That is, as noted in the incorporated patents, the described measurement methodology takes advantage of the fact that individual THM species produce a red optical color at different rates (e.g., of the four THMs, chloroform reacts most slowly, whereas the next most similar species bromodichloromethane gives the fastest reaction rate). The reaction rates and color intensities profiles are typically pre-determined for each THM (or combination of THM) on each individual analytical apparatus used for measurement, and these calibration parameters (Fujiwara colour intensity at specific reaction times for each THM) are then typically stored for use in speciation measurement. Thus for any given water sample, individual THM concentrations can be derived 419 by first making multiple colorimetric absorbances measurements at the appropriate times over the course of that Fujiwara reaction (e.g. 130, 500 and 1200 secs), and then by solving the set of simultaneous equations using the known THM calibration coefficients, in view of the absorbances just obtained. The sample's THM quantity information together with other measured data and analysis methods can be used to forecast DBP concentration levels at other temporal or spatial points in the distribution network (or an equivalent sample isolated from the network but aged in the laboratory under conditions that simulate the network); these measurements can also be factored into the learning process 423. Furthermore, as noted by numeral 422, averaging/blending of measurements with a window of adjacent samples is advantageously performed to simulate accumulation of water over time.

The described processing provides an accurate way to measure DBP concentration on an real-time or near real-time basis, as well to predict DBP levels at various times/points in the water distribution network. Using measurements and level forecasting in this manner, proactive corrections and/or process modifications can be made to reduce the levels of and/or avoid the presence of DBPs before water is distributed to the consuming public. Additionally, a water supply can take actions such as performing less filtering or changing water source reliance, so as to make water distribution more cost efficient. For example, returning once again to the introductory example provided by FIG. 1, if water from the depicted reservoir 103 was determined to have very strong DBP formation potential, potentially given other environmental factors (e.g., "month"="July"), the subject water supply could choose to switch to well water delivery, to otherwise reduce the flow rate of water from the depicted reservoir 103, or to increase filtration or other processes (such as depicted by numerals 109, 111, 113, 115, 127, 129 from FIG. 1). Many other actions/reactions are possible, as noted.

Figure 4B:
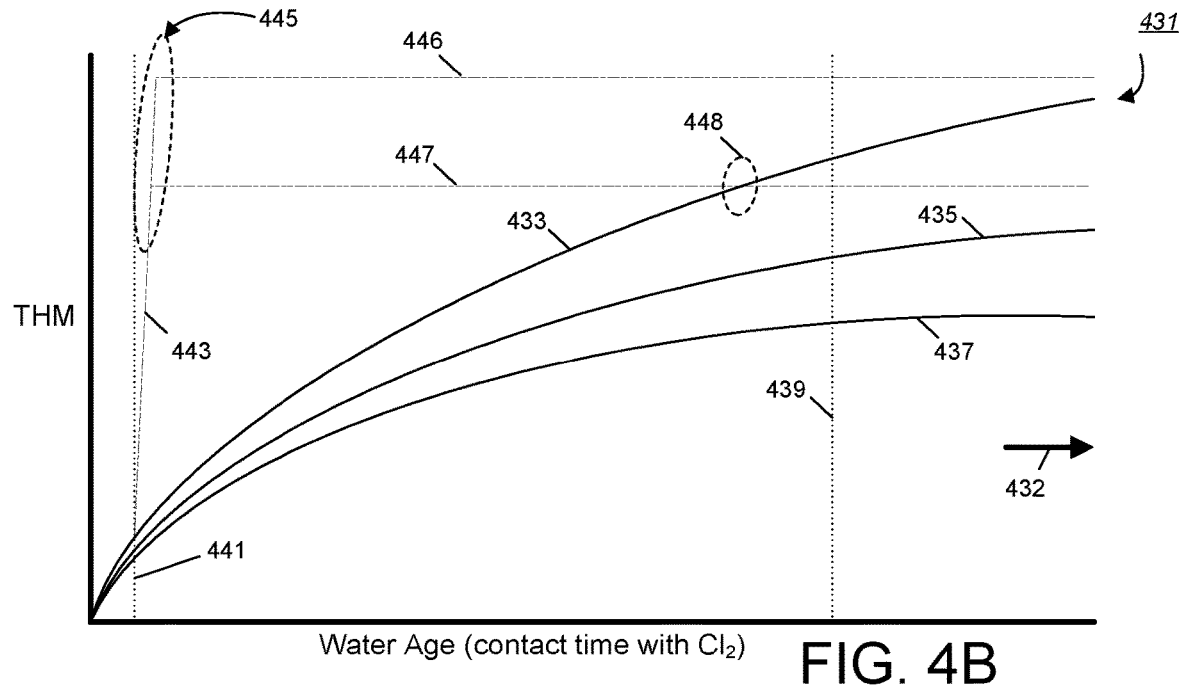
FIG. 4B is a graph 431 that shows three hypothetical curves, 433, 435 and 437, each curve representing different THM formation characteristics given variables associated with a water supply and treatment activities, such as water temperature or chlorine doing levels.

FIG. 4B shows a graph 431 of three hypothetical curves showing THM formation as a by-product of sanitizers in water; generally speaking, the longer a given water sample contains chlorine-based and bromine-based sanitizing agents, the greater the THM formation in the water. Breakdown of the sanitizers over time can also be a function of many variables that can affect a water supply, such as water temperature, exposure to sunlight, flow rate, exposure to other materials (e.g., metal pipes or other compounds present in the water), and potentially many other factors. FIG. 4B shows three hypothetical curves, 433, 435 and 437 that each represent different rates of THM formation over time. [It should be assumed that there are potentially an infinite number of such curves, with only three being illustrated for purposes of discussion.] The vertical axis at the left of FIG. 4B represents THM presence at time t=0 (i.e., when chorine for example is added to water to disinfect the water), and the horizontal axis represents time following introduction of the chlorine, for example, expressed in days. It should be noted that FIG. 4B is drawn for purposes of illustration and is not necessarily drawn to scale. Two vertical lines represent possible times of interest, e.g., line 439 represents THM development at an arbitrary time of three days (72 hours) after chlorine introduction, while line 441 represents a potential in-facility measurement time of one hour after chlorine introduction. It should be assumed that THMs are produced as a time-based function such as represented by curves 433, 435 or 437, but that the specific curve that accurately models THM formation is unknown; it should further be assumed that THMs (and/or other DBPs) will continue to develop up to a maximum value at some point after treatment (e.g., potentially after drinking water has left the control of the water supply), as represented by arrow 432, off to the right side of the FIG. It is typically desired both to understand maximum DBP development and also provide for appropriately sanitized water at the time of delivery of water to a consumer.

The techniques described in this disclosure use preselected age acceleration parameters to forecast formation potential for a given facility, a given DBP, and given temperature and other aging assumptions. These parameters are employed at the time of measurement to accelerate DBP formation and thus simulate water aging in a manner that can be used to forecast both amount and time of maximum DBP formation (e.g., on a species-specific basis). To this end, as introduced above, a captured water sample is heated prior to THM extraction, in order to deliberately break down added sanitizers in a controlled manner and produce THMs on an accelerated basis; for example, if it is assumed that curve 433 accurately represents THM formation for a specific municipality over a certain period of time (e.g., a certain time of day, of a specific month in a specific season), the techniques described herein accelerate aging of the water sample in a manner consistent with line 443, using heat according to a predetermined temperature profile for a specific period of time. Note that a single temperature can be used, multiple temperatures and respective heating times can be used, or any other form of temperature profile can be used, to simulate THM formation at a future point in time. If numeral 448 for example represents a period of two days (forty-eight hours out) and it is desired to forecast THM formation at that point in time, then the reaction is halted as represented by ellipse 445, in a manner that freezes THM development in a manner corresponding to the selected time, per horizontal line 447. In this case, for example, a dechlorinating agent is introduced to a water sample to remove residual chlorine from the water sample (i.e., without affecting THMs already formed in the sample) and the sample is then measured in real-time (e.g., using a 20 minute measurement cycle) to measure THM species present at that time. Similarly, if it is desired to forecast THM formation at another point in time (e.g., 5 days out), the heat profile is slightly different, with the reaction allowed to proceed at a slightly longer time, with the dechlorinating agent then added to freeze THM development in a manner corresponding to that time, e.g., at the level represented at line 446. By empirically (or regressively) choosing both the temperature profile and associated times, and correlating these with variation in environment variables and empirically measured THM levels (based on stored, aged water samples), the temperature profile can be selected and refined so as to accurately model future DBP development (i.e., for THMs specifically in this example); this will be further discussed below in connection with FIG. 7.

FIG. 4C shows a graph 451 that illustrates typical variation in formation potential for any given water supply as circumstances change; in this FIG., the vertical axis represents DBP (THM) concentration (aggregated across THM species) in units of micrograms per Liter of water (ranging from 20 to 70, as demarked by horizontally-extending grid lines), while the horizontal axis represents time in days (with each vertical grid line representing a day); the graph 451 represents about six measurements per day, equally distributed throughout the day. As can be seen, predicted THM formation can vary widely, owing to factors such as water flow rate, time of day, temperature, season and other factors. Note that the raw measurement data itself may not accurately represent DBP levels at any specific point in the water distribution network, it represents DBP formation and decay that is expected from a given water sample at a specific future time, with a typical presumption that water corresponding to the sample was/is handled under the same (temperature and other) assumptions. However, in a typical WTP or water distribution network, continually-changing water is typically accumulated over time in storage tanks and elsewhere within the network; in other words, a more accurate formation potential prediction is obtained by combining multiple measurements in a type of convolution, i.e., dependent on average age of water at a given prediction point based on a water contributed at many different points in time, and depending on a function applied to a possibly-dynamic range of weighted samples. In the represented embodiment, therefore, a digital filter is applied to a window of measurement results (and potentially measurement results representing plural sources) to predict actual DBP levels based on weighted combination of multiple formation potential measurements, and potentially other data. In one embodiment, the filter accounts for time-wise adjacent measurements using weighting that is a function of average age of the water at the prediction point relative to the measurement point. For example, the filter can average or blend a group of measurements representing a relatively wide time window when the average age of water is relatively long, and a narrower time window when the age is reduced, i.e., accounting for greater turnover and less blending of the water, with emphasis for a specific measurements based on variation in flow rate. A plotted, dashed line appearing in the FIG. represents the effects of this blending and is found to closely model true (observed) DBP formation. As implied, the function implemented by the digital filter in one embodiment is varied depending on environmental variables, including without limitation season (e.g., implied water usage/turnover), day, time, month, flow rate variation, mineral content, pH, and any other desired environmental or water delivery variable. By understanding and being able to accurately forecast variation information potential at any point in time, it becomes possible to take action at the water supply or elsewhere in the distribution path in order to better control DBP formation.

FIG. 4D shows a flow chart associated with the forecasting process; an in-situ detection mechanism such as described above can be used for purposes of measurement, according to steps generally represented by numeral 461. More specifically, a measurement frequency is programmed 463 into memory for the in-situ detection mechanism, with resident software then being controlling the measurement cycle (and cleaning/renewal cycle) according to the programmed frequency; for example, as alluded to above, measurements can be taken automatically by the in-situ detection mechanism every hour, if desired. Per numeral 463, the programmer can program this frequency into a register of a specific in-situ detection mechanism (e.g., "hourly"). The programmer optionally programs desired target age into memory 464 for use in selecting the accelerated aging process to be used to measure formation potential; in one embodiment, this value can be fixed or represent a standard (e.g., seventy two hours after sanitization) and, in other embodiments, this value can be set ad-hoc (e.g., by command operand) or made to be automatically variable according to factors such as water flow rate (e.g., the faster the water flows, the shorter the presumed time until water is delivered to a consumer). Once the in-situ detection mechanism has an understanding of these parameters, it then automatically performs measurement 465, logging and/or reporting of environmental variables for logging (e.g., date, time, temperature, flow rate, etc.). In one embodiment, the in-situ DBP detection mechanism can accesses forecasting parameters which have also been stored by in the system database (466); these parameters can, as mentioned, optionally result from a learning algorithm which continuously updates the parameters based on historical data measured for the specific water supply at issue, or based on predicted environmental variables. These values are then applied to forecasting 467 with forecasts being logged or reported to an operator. Per numeral 468, such forecasting can represent a myriad of variables, to provide for an accurate DBP/THM concentration predictions. Per numeral 469, alerts and/or controls can be generated as a response to such forecasts/predictions. In one embodiment, as referenced by numeral 470, each prediction and/or measurement can be stored in the form of a standard template; that is, as will be further explained below in connection with FIG. 6A, in one embodiment, a normalized or common communications or data exchange format is established to provide one or more normalized structures for exchanging and storing data. Per numeral 471, stored measurements and forecasts can thereafter be applied to new forecasts and to periodically updating prediction models, as referenced elsewhere herein.

FIG. 4E shows a table 485 providing hypothetical water quality data, e.g., such as might be reported by in associated with a water source or generated monitoring equipment (including one or more in-situ DBP detection or other monitoring mechanisms). As seen in this FIG, a report for a particular water source (i.e., a water treatment plant) reports data at discrete periods of time, i.e., on an intermittent basis, such as every hour, every four hours, etc. Such data can be logged in template form, as discussed below. In the example seen in FIG. 4E, the upper three-quarters of the table represents parameters reported by the water supply (source), for example, with respective fields as indicated for pH, total organic carbon (TOC), WTP chlorine dosage, bromide levels, acceptable concentration range for a one or more DBPs (e.g., TTHM in this example), water hardness, total alkalinity, a seasonal temperature or temperature range for fall/winter, a seasonal temperature or temperature range for spring and summer, and so forth. The lower quarter of the table represents in-situ measurements at another location in the water distribution network, for example, residual sanitizer detected to be present at the sampling point ($Cl_2$), measured DBP (e.g., TTHM) and average water age relative to source.

FIG. 4F shows some variables or parameters that used to define DBP concentration prediction for a single water source. Preferably, software is preprogrammed to look at a number of factors, and performs prediction based on the listed parameters in order to estimate DBP concentration; variables used in one embodiment are represented by numeral 491, and are seen to include water temperature, site of measurement, date, time, water composition (e.g., metal constituency), flow rate, tank level, age of the water (relative to sanitizer introduction) at the time of measurement, heat levels to be applied in i discrete heating cycles, each for a respective duration, and a function to average formation potential measurements. Note that any desired function can be implemented as desired, e.g., if measurements are taken every hour, it might be desired to use a digital filter as described to perform a weighted analysis based on the immediately previous five samples and the sample taken at the same hour the previous day (or previous week); many examples are possible and will readily occur to those of ordinary skill in the art, and fewer, more or different variables can be considered, depending on embodiment.

Figure 5B:
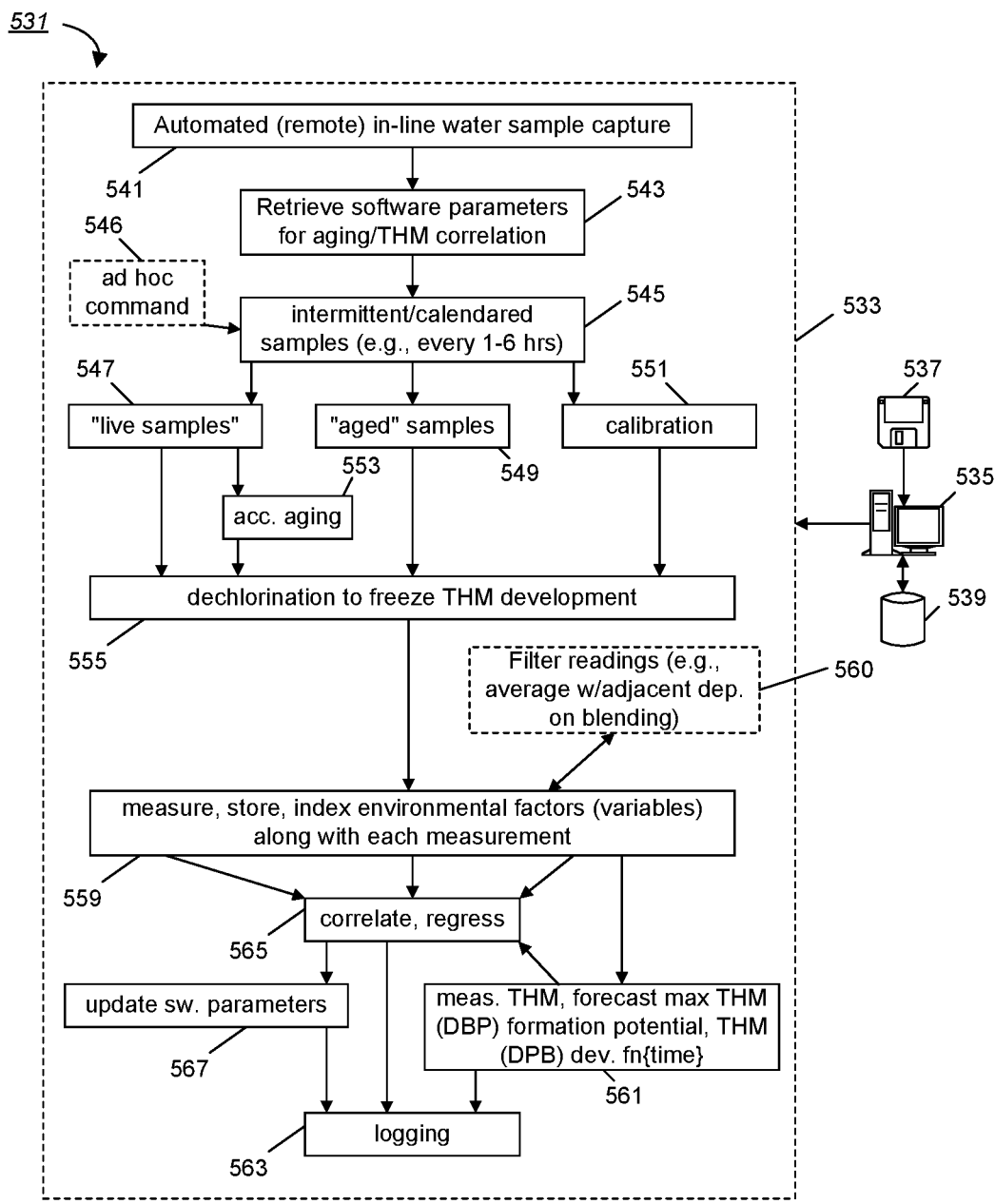
FIG. 5B provides a flow chart 531 relating to forecasting DBP formation, specifically, for THMs.
Figure 6A:
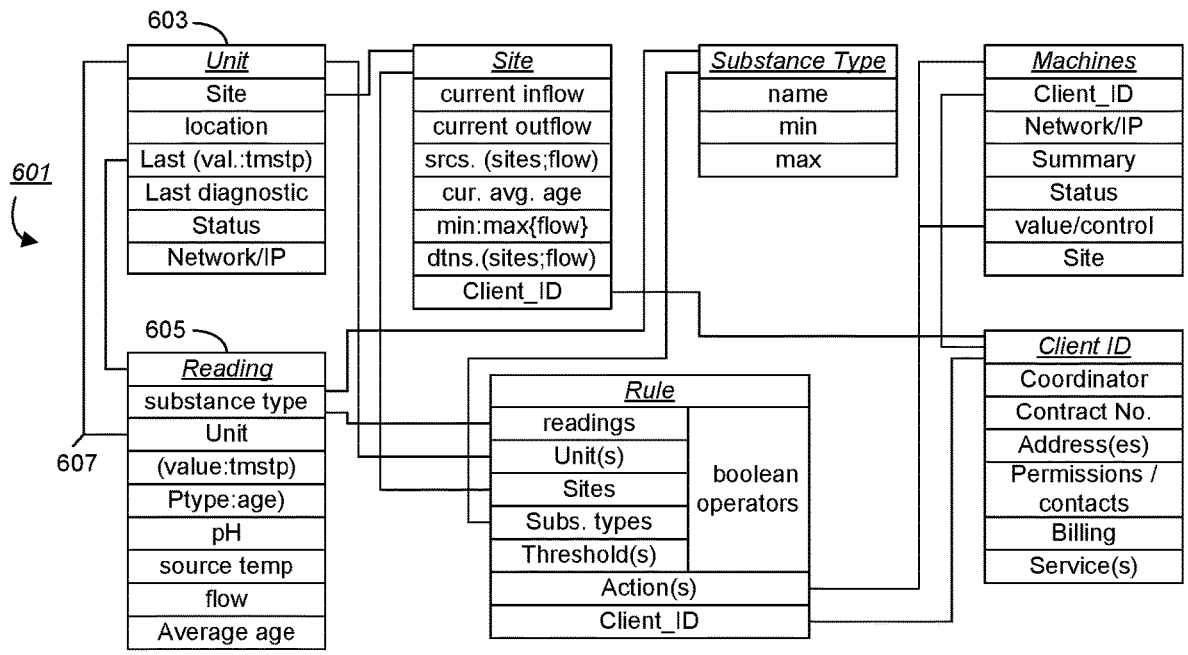
FIG. 6A is a layer diagram showing hardware, software application, object and scripting layers associated with one or more computers of a water monitoring network.
Figure 6B:
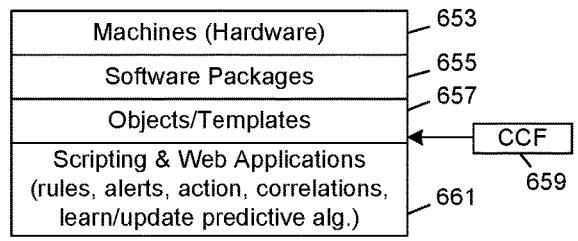
FIG. 6B illustrates a set 621 of exemplary templates, used by a relational database structure for logging water quality data and environmental variables, for purposes of correlation and prediction according to the methods herein.
Figure 6C:
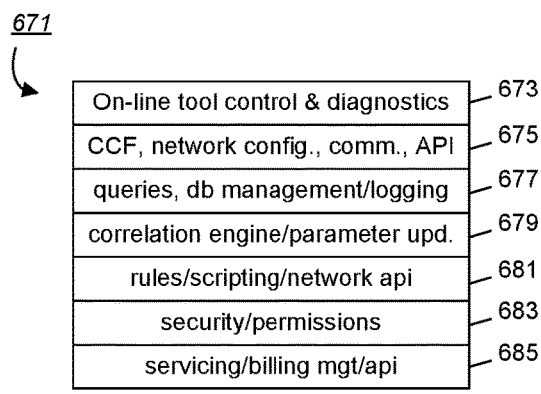
FIG. 6C shows a block diagram 671 of exemplary software modules, which may be embodied as instructions stored on machine-readable media for controlling one or more computers, processors or other digital devices.

FIGS. 5A-5C are collectively used to provide additional detail regarding a water monitoring network that interfaces with one or more in-situ DBP detection mechanisms. FIG. 5A relates to the operation, in one embodiment, of each in-situ DBP detection mechanism, FIG. 5B provides detail regarding one embodiment formation potential measurement by either of an in-situ DBP mechanism or water monitoring network, or both cooperating together, and FIG. 5C provides detail regarding an implementation of the water monitoring network.

FIG. 5A introduces an embodiment 501, including a business method, of operating an in-situ DBP detection mechanism. In particular, such a mechanism may be used to test for at least one halohydrocarbon (THM specie), based on a modified Fujiwara process as introduced above and as reference by numeral 503. Because traditional Fujiwara chemistry can involve noxious fumes, a modified chemical process is used which relies on substitute or modified chemistry, as referenced, and helps limit worker exposure to noxious fumes or hazardous chemicals; this therefore facilitates design of an in-situ detection mechanism that can be used at water supply facilities, with infrequent servicing by water supply personnel. Based on samples drawn and measurements taken in-situ, concentration of at least one halohydrocarbon in a sample is locally determined, per numeral 505. As referenced previously, dosing and/or sample preparation steps can optionally be performed 504 before measurement, for example, to measure absolute or relative effects of dosing or treatment on raw or previously processed water samples. Results of measurement may be electronically stored in a database, indexed by a time stamp and any other environmental factors deemed pertinent (e.g., water temperature at sampling), and a log may be generated for demonstrating regulatory compliance and for detecting situations when monitored substances exceed desired levels, as alluded to by numeral 507. These results are also advantageously used with environmental data 508 and applied used for prediction of DBP levels at desired times and/or locations in the water distribution network.

FIG. 5A also references several optional steps. First, per numeral 509, pyridine derivatives can be used for the referenced substitute chemistry, facilitating the goals of relatively safe chemicals and local maintenance, e.g., materials used for the reaction may be stored in local reservoirs and occasionally replenished, with waste materials being collected and safely disposed. As implied above, relatively easy maintenance facilitates in-situ systems without requiring extensive training of personnel. Second, per numeral 511, materials that degrade over time may be recalibrated and used until they need to be replaced using one or more locally stored calibration media (i.e., one or more "standards"). As discussed in U.S. Pat. No. 9,134,290, for example, an electronic control system may be used to run the same steps used to test the potable water supply with each locally stored calibration test medium (e.g., on THM-free water); self-calibration further enhances the ability to provide and effectively use in-situ devices for monitoring chemicals such as THMs. The same is true for automated renewal processes that, following one measurement, purge residual THMs from extraction media and measurement equipment, and prepares the detection mechanism for a new cycle of measurement. Finally, per numeral 513, for embodiments that use computer control of the various sampling and testing steps according to a predetermined schedule, a LAN or internet connection 514 may also be provided for transmitting measurement results to a central monitoring facilities, e.g., the water monitoring network of FIG. 5C, or a regulatory agency, regional water management station, or some other type of entity. This operation facilitates continuous monitoring of actual and/or forecasted chemical levels and fast formulation of responses to problems. In this case, data from the particular in-situ detection mechanism can be indexed by various factors, including unit serial number, time of measurement, particular THM values, other water quality data (e.g., chemicals/organics present, temperature, pH), location, etc. This data may be logged either in a dedicated file or, in connection with the network of FIG. 5C, as part of a database used to track several of the in-situ mechanisms. If desired, the determination of THM amounts (or other DBP amounts) may be compared to one or more thresholds, as indicated by dashed line "options" block 515, and a reaction such as an alert 519 may be generated if concentrations exceed desired level; alternatively, per numeral 521, an electronic control system may responsively and automatically adjust upstream water treatment processes via the generation of automated machine control values, i.e., to either increase or decrease the use of certain chemicals, or to provide for a sanitized water supply that will not exceeding recommended norms (either presently, or prospectively). Individual DBP species' contributions may also be used in diagnosing issues associated with the water treatment process.

FIG. 5B provides a flowchart 531 used to explain calibration and measurement of formation potential from a control perspective (e.g., either the perspective of a control system and/or software for an in-situ DBP measurement system, or from the perspective of a remote water monitoring network). Software functions in performing this analysis are generally represented within the confines of a block referenced by numeral 533. These functions can be performed on a computer 535 having one or more processors that are controlled by instructions stored on non-transitory, machine-readable media, or by other types of circuitry. The computer or processors can manage one or more databases 539 (e.g., data stored in non-transitory memory), including without limitation a database that stores environmental variables associated with each water measurement, forecasted and actual DBP species' concentrations, and other parameters.

More specifically, as represented by numeral 541, this software controls operation of the in-situ mechanism including actuation of mechanical elements to perform water sampling, aging and response development. As each new sample is to be measured, the software loads parameters (e.g., coefficients) that will be used for measurement and forecasting 543. Note that, as referenced above, these coefficients can be varied over time as water samples are taken, according to regression or feedback resulting from the comparison of forecasted values and measurement of aged samples. Per numeral 545, the software advantageously controls measurement on a calendared basis, for example, performing automated sampling, cleaning and systems renewal every 1-6 hours; this can result in 4 or more samples taken daily. As denoted by a dashed line block 546, control can also either be ad hoc, originating from control software 537, in response to occurrence of a triggering system event (e.g., scripted in response to other measurements), or as commanded by a human operator or a remote water monitoring network. Numerals 547, 549 and 541 represent three different processes that can then be performed: First, per numeral 547, the system can be used to process "live" samples, representing water samples instantaneously drawn automatically from the water supply that are to be measured right away for DBP presence or formation potential; Second, per numeral 549, the system can also process aged (stored) samples, e.g., water drawn by the system 2-3 days earlier (or at another prior interval) which are currently to be measured for DBP presence, with the results being compared against previously forecasted values (i.e., based on another, previously processed sample of the same water), and used to adjust forecasting parameters (coefficients) or the heat profile used for formation potential measurement, as appropriate; Third, per numeral 551, samples can also be drawn for purposes of system calibration, e.g., water from the actual supply being measured can be drawn, purged of disinfectant (and THMs), subjected to addition of a known amount of THMs, and then measured to calibrate the system, e.g., using a "spike test" as described by U.S. Pat. No. 9,134,290. Whichever process is performed, the sample in question is then heated 553 according to a predetermined temperature profile, as referenced previously; it is expected, given typical water supplies (e.g., municipal water supplies) that these heating profiles will be on the order of 50-70 degrees centigrade for thirty-to-sixty minutes. In other embodiments, these values are different.

As noted previously, the heating is performed to accelerate DBP formation and artificially age the water sample relative to the water source being measured. In one embodiment, the sample volume drawn for each sample 541 can be enough to fuel multiple measurements, for example, with each measurement iteration simulating a different age, so as to trace out a DBP formation and decay profile corresponding to the given sample. For each measurement iteration, once the desired amount of heating/aging has been applied, the DBP formation process is then halted, e.g., by the addition of a de-chlorination or other agent 555 to remove the chemicals that contribute to THM formation. With DBP formation potential values (e.g., including TTHM and individual species' concentrations) computed for each desired water age and each desired water source, such data can then be applied to develop a heat profile that will be used to determine how samples are processed such that artificial aging represents a selective age; this will be further discussed below in connection with FIG. 7. Once calibrated, the system can be used for measurement of formation potential with measurements factored into predictive analysis with either internal data or external data (e.g., any pertinent environmental data) and used to assess the efficiency of the water distribution 561; once again, all predictions and measurement results can be logged, per numeral 563. For example, in one embodiment, one or more formation potential measurements can be supplied to a predictive algorithm based on variables such as temperature, date, time of day, water flow rate, and other variables, and used to predict actual DBP concentrations at a specific location and/or time in the network, based upon the various environmental or other variables used to model DBP concentrations. As part of this analysis, as discussed earlier, multiple readings taken at respective times can be averaged or weighted in dependence on a window of adjacent samples to adjust for blending of water in the water distribution system or in specific storage tanks or units 560. Predictions can be compared against actual values and the variables used, e.g., correlation and regression 565 can be performed by software so as to improve the statistical accuracy of the predictive algorithm applied by software and update coefficient variables and/or the aging used to measure formation potential 567. Logging of measured formation potential, the values of variables used in the predications, and measurements of DBP presence in fact are advantageously made part of the logging process 563, with logged data either being stored locally or sent via LAN or WAN to a remote database 569.

Reflecting on the principles just discussed, software tracks historical data on formation potential forecasts and associated variables, and performs a running or intermittent correlation/regression, to improve the accuracy of DBP formation potential measurement and forecasting of DBP concentrations at specific points in the water delivery process.

FIG. 5C shows another embodiment 571, this time from the perspective of a water monitoring network. As seen in the FIG., one or more processors 573, acting under the control of suitably configured software, manage database logging and storage functions, and perform routine database maintenance functions 575. Data readings from DBP prediction efforts from in-situ DBP measurement systems are received and stored in the database 577, generally with a time stamp and an identifier as to the specific unit that produced the measurement, and associated data describing water quality. In one embodiment, records are received and/or compiled as standard objects or database templates suitable for use in a relational database or equivalent. Measurement data can be received from via a LAN or WAN interface 579, for example, as relayed through the Internet (represented by a cloud icon) by a multitude of in-situ DBP detection mechanisms (or other systems) and/or clients 581, for purposes of logging and/or prediction and/or water monitoring.

The one or more processors implement a monitoring engine 582, a prediction engine 583 and a correlation engine 585. The monitoring engine 582 implements tasks and alerts according to scripted rules, for example, taking an action dependent on a DBP reading, or as a function of multiple readings, satisfying a particular threshold. The prediction engine 583 performs prediction of DBP concentrations based on data reported from the in situ DBP detection mechanisms and desired environmental variables according to rules scripted for the particular water supply; for example, if the pertinent water supply was a municipal water supply with aqueduct and reservoir water sources available and a specific configuration of storage tanks, the prediction algorithm would be coded so as to be based on these sources and tanks and associated environment variables for that specific delivery network. The correlation engine 584 is used to update prediction models 597 (and associated coefficients or operators, and/or aging profiles used for formation potential measurement) using regressive or best fit analysis 595, e.g., so as to improve prediction based upon variables applied and correlation with measured true DBP values.

A number of reactions can generally be implemented on processors 573, typically be a dedicated software application or by suitable scripting. For example, as referenced by numeral 587, alerts can be automatically generated in response to rules that operate on the pertinent environmental data, measurements of formation potential and/or predictions of specific DBP concentrations. For example, if DBPs are predicted to exceed safe norms, given predicted formation potential and expected temperatures, an alert can be automatically triggered to a human operator that advises that additional water treatment procedures should be applied (e.g., to reduce organics presence in pertinent water sources). As noted earlier, there are many possible reactions that can be taken, and alerts can be used to general telephonic, email or other messages to specific human operators. As indicated by numeral 589, rules can also be used to trigger automated actions, for example, invoking automated water treatment processes, changing treatment parameters (such as disinfecting agents used or associated concentrations, regulating flow, and potentially other actions). Such reactions can be based on programmed parameters 598 that take into account the cost analysis 599 pertinent to a given water distribution system.

As indicated by numeral 593, a water monitoring network also advantageously supports a query engine and API for interacting with the system/network; for example, the one or more processors 573, acting under control of suitable software, implement an API that permits a human operator to query for any desired historical record, to command ad hoc DBP or other automated water quality measurements, to change prediction models, command calibrations, and take other actions.

Numeral 594 references a service engine 594, denoting that the functions depicted in FIG. 5C can in one embodiment be operated on a service bureau basis. That is, in one contemplated implementation, an entity may provide water monitoring services for one or more clients. Each client for example can be a municipal water company or other water supply having one of more in-situ DBP detection mechanisms. The water monitoring network provides a secure portal (i.e., in association with the WAN interface 585) that permits administrators or proxied users for each client to log in, view data, and establish rules for automated responses and alerts. The responses and alerts, not to mention DBP prediction services, can be provided dependent on a subscription by the particular client, e.g., each client installs water measurements systems that automatically interact with the network software using push/pull functions to report/collect measurement data. In such an embodiment, the client can script rules ranging from periodic notifications (e.g., hourly emails or downloads of ever changing formation potential data), to alerts of conditions based on client-established parameters, to automated machine commands to change processes or control values. The water monitoring network implements the functions seen in FIG. 5C while each client installs in-situ DBP detection mechanisms (and other measurement mechanisms) and employs client-side software to interact with the water monitoring network. Each detection or measurement mechanism can optionally be configured for direct network access if desired, so that data can be directly exchanged with the water monitoring network or the client's network, as pertinent to the installation.

As noted earlier, in one contemplated implementation, DBP measurements taken at periodic intervals and formation potential measurements taken by in-situ detection mechanisms are logged, e.g., with a time stamp and potentially other water quality data and information identifying the measurement source, for purposes of forecasting/prediction, and potentially for reasons of accountability as well. FIG. 6A is used to discuss one possible framework 601 for such an implantation, e.g., where an object model or relational database architecture is established for storage of results and some of the processes described earlier. FIG. 6A represents a schema of object properties or relational database fields that might be used to provide service bureau activity by an enterprise, but can also with suitable adaptation be applied to a closed network (e.g., such as the network of a large municipal water company). Note that the schema presented by FIG. 6A is exemplary only, i.e., one skilled in the art can select other fields or properties to use, depending on circumstance or implementation.

As seen in the FIG. a number of templates are defined, such as template 603 or 605, with each listed value representing a property or field that would be stored as part of an instance of each such object or database record. As an example, the template type "unit" (603) is seen to have properties/fields of "site," "location," last reading ("Last (val.:tmstp)"), "Last diagnostic," "Status" and "network/IP." As implied, such a record would be used to identify each in-situ detection mechanism in the field, respectively identifying (a) a unit number or serial number, (b) a number, address or other identifier indicating the site at which the particular unit is installed, (c) where the unit is installed at the indicated site, (d) last produced reading, including value, and timestamp, (e) current operating status, and (f) a network ID (e.g., the electronic address that can be used to communicate with the device). By contrast, the template type "reading" 605 is seen to have properties or fields indicating a reading number (e.g., a unique ID), substance type representing the substance measured by the device (e.g., "TTHM"), a "unit number" which identifies the in-situ detection mechanism which produced the particular reading, the value/timestamp associated with the particular reading, a prediction type (e.g., current THMs present/age=0, versus a formation potential forecast/artificial aging in hours), and other pertinent water data, such as pH, source water temperature, flow, and average water age. Once again, these properties/fields are illustrative only, and any suitable properties or fields can be used as desired for the pertinent implementation. Note that for templates 603 and 605 that the property/field "unit" is shown connected by a line 607; this denotes that this property is linked for the two referenced template or object types. As an example, if a database record for a reading indicates a value of "004" for the field or property "unit," this value can be used to access the "unit" template or object having a record number/property "004" and to retrieve information for the individual unit which produced the particular reading. That is, there may be many "readings" produced by unit "004" over time (all logged), and the value "004" can be used as a unique identifier to bring up information on "that" unit which produced these many readings, e.g., sorted by time of reading or other criteria. Returning briefly to FIG. 5C's reference to a query engine/API 593, it is noted that this type of architecture provides an infrastructure for servicing a wide variety of queries; as implied by this example, in one embodiment a hypothetical query can seek a return of all readings (or readings for a specific time or date range) produced by a specific unit. FIG. 6A depicts many other possible templates or object types, for example, one for "site" (e.g., indicating specifics associated with a particular point in a water distribution network, such as a facility, water source, storage tank, and so forth), one for "Rule," (e.g., having properties/fields that can be crafted to invoke automated actions when specified conditions such as Boolean conditions are met relative to specified thresholds or values), "Substance Type" (e.g., specifying each individual substance that is to be measured or otherwise used as the basis of a rule, e.g., each DBP species being measured and/or monitored), "Machines" (e.g., non-detection mechanisms such as water treatment systems, valves, diverters and the like that can be used for automated control and/or reaction), and "Client_ID;" other templates and/or properties/fields can again be used as pertinent to the particular implementation. Note, relative to implementation as a service bureau, that the "Client_ID" template can be used to associated sites, rules and machines (and potentially other templates) with respective clients; for example, in one implementation, an enterprise performs online water monitoring functions on behalf of multiple clients (e.g., respective municipal water companies or other water supplies). Each client has an associated address, designated administrators and permissions backed by cryptographic credentials, and the service bureau receives automated "push" readings (or alternatively, performs polling) as configured by or for the particular client for in-situ detection mechanisms managed by that client (e.g., for potentially multiple THM, HAA or other DBP detection mechanisms used by that client). In turn, each client uses a secure web portal to run queries on that client's reported data and measurements, and to establish rules/scripts specific to that client and that client's available machines that take client-specified actions when client-specified thresholds are reached. As an example, one client may elect to establish rules with the service bureau which generate email alerts when certain thresholds are reached (e.g., predicted formation potential for any source for a selected water age is found to be greater than a threshold, or peak formation potential at any age if found to be greater than a threshold), while another client might instead elect to automate responsive machine control as a function of its rules. To this effect, the various rules in one implementation can be used to initiate automated machine commands directed to the particular client's machines using the machines templates, e.g., effectively, the client configures the service bureau to, as a response to client-reported data, issue a TCP/IP-based command directly to a network address associated with a specific one of the client's machines to initiate a control activity, for example, changing a chemical level, or a flow rate, or diverting water to a different flow path or treatment process. Once again, these examples are illustrative only, and it should be again noted that these various techniques are not restricted to service bureau application and can be instantiated in a closed network. It should appreciated that the described framework permits many different types of automated and/or other responses, dependent on detected DBP levels or predicted formation potential.

FIG. 6B shows a layer diagram associated with a water monitoring network. Per numeral 653, hardware is allocated at a machine level to perform the various processing described herein, for example, one or more computers, servers or other digital devices. In one implementation, such a machine or machines exchange communications by WAN with one or more in-situ DBP detection mechanisms and one or more other devices used for water quality control, supply or processing; in one implementation, some of the functions described herein may be made viewable or interactive via one or more mobile devices, for example, the receipt of operator queries which can then be run against database entries. In another variation, each hardware machine can include one or more virtual machines running on hardware. Numeral 655 refers to a software layer, where one or more custom software applications (e.g., a database and logging application, or a correlation and regression application) can be installed to run the various tasks as described herein; as will be discussed further below in connection with FIG. 6C, a number of different functions, programs, routines or software modules can be provided for to perform the various described functions as pertinent to the desired implementation. Numeral 657 refers to the use of objects/templates and associated properties and fields, for example, as discussed above in connection with FIG. 6A; as indicated by numeral 659, preferably, these objects/templates/properties/fields implement a common communication format ("CCF") for exchange of data between multiple machines and operators, and optionally, to reconcile potentially different data reported by different types of monitors/detection mechanisms used to monitor respective DBPs (i.e., such that data can be imported/translated to a standard format). Per numeral 661, a scripting or web-application layer permits rules and automated responses to be developed and invoked when specified conditions are satisfied.

FIG. 6C shows a collection 671 of software modules that can be used in one embodiment. As noted earlier, each software module consists of a dedicated code set for performing an associated task. A first module 673 is seen to provide for on-line/in-line tool control and diagnostics, e.g., control over an in-situ DBP detection mechanism; for example, as referenced earlier, in one embodiment, such a tool receives programming to establish various parameters, such as frequency of automated measurement, or to ascertain levels of various consumables remaining, or to perform a calibration, ascertain machine status, obtain last reading, take an ad hoc measurement, set a selective age or assumed average temperature for which formation potential is to be measured, and so forth. The on-line/in-line tool control and diagnostics module is used, simply stated, is used to provide an interface between each in-situ detection mechanism and a remote network and/or a human operator. A second module 675 provides for functions relating to the CCF, network configuration, communications and an API for the database scheme; for example, such a module can be used to modify the database schema so as to interface with new control or monitoring equipment in a given water distribution network (including as to the definition of network address), or to expand data reporting so that new variables can be reported and linked to measured data. A query/database management and logging module 677 provides an interface to the reported measurements, forecasts and other data logged by the system; for example, such a module advantageously provides an API for query support of the database. Yet another module 679 provides for correlation functions, regression and parameter update; as an example, it was earlier mentioned that in one embodiment, as the amount of logged data increases (potentially including predictions and corresponding verification measurements), the prediction and/or formation potential aging algorithms can be refined to improve accuracy, for example, through the use of regression to improve correlation between certain environmental variables and formation potential measurements with measured DBP concentrations at a specific point in a water distribution network. A sixth module 681 permits a given network to implement scripting, rules or software functions to cause the water monitoring network or machine to take specified action in response to measured/forecasted data; for example, as alluded to earlier, such a module permits a particular water supply to specify that certain actions (e.g., notifications, alerts, automated machine control) be taken when in-situ DBP detection mechanisms generate particular readings, or when certain DBP concentrations are predicted. Numeral 683 refers to a security/permissions module, e.g., which allows a network to specify which login credentials are needed to access certain data, run queries, generate reports, or perform network/machine administration functions. Finally, in the case of a service bureau, a servicing module 685 implements functions relating to billing management and services selection for the particular client.

As should be apparent, the various network and/or machine architectures described with reference to FIGS. 5A-6C are exemplary only; nevertheless, they help illustrate a variety of different machine and/or network and/or service-based implementations that can make use of the DBP measurement and formation potential prediction capabilities introduced earlier.

Figure 7:
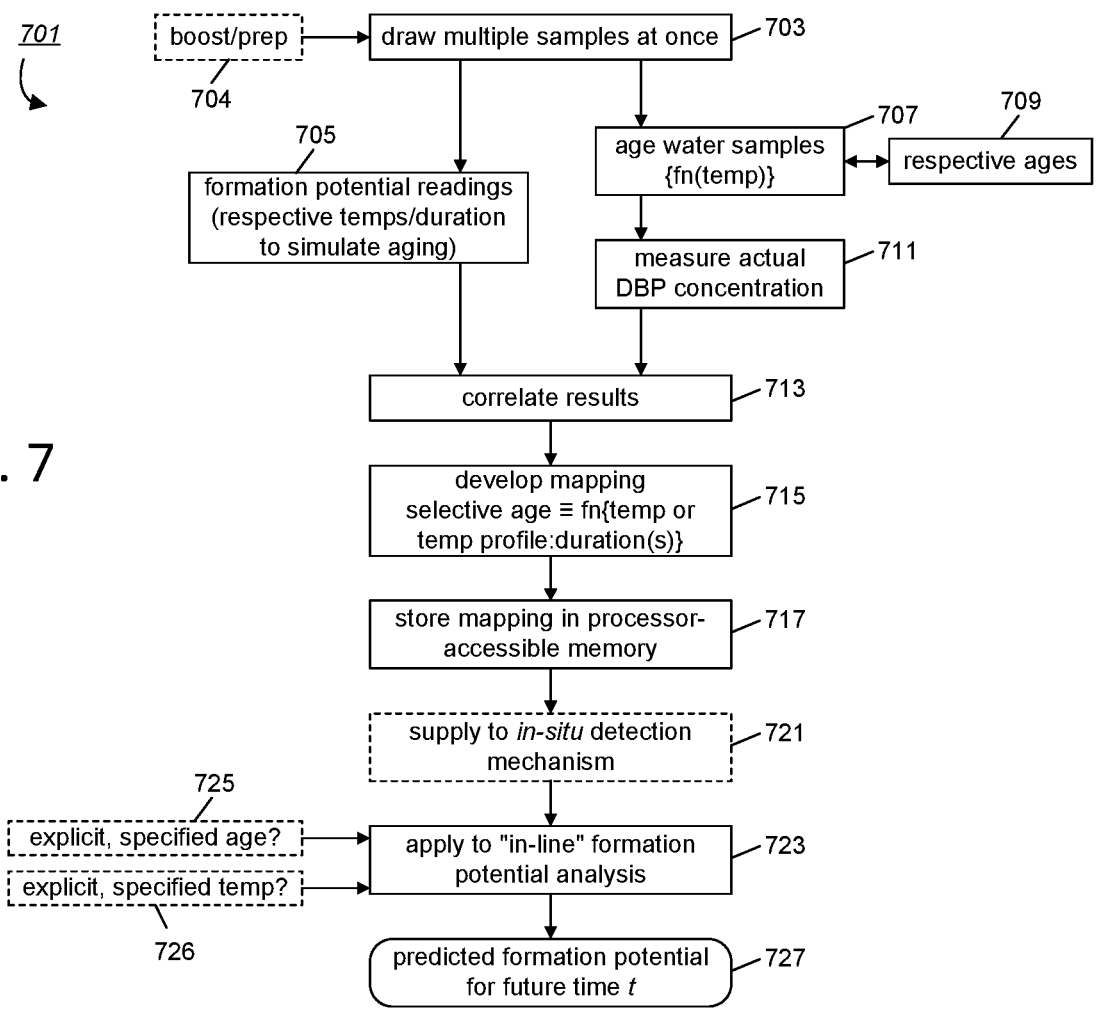
FIG. 7 shows a block diagram 701 of a method of mapping desired age to a specific temperature/duration (or temperature profile, and durations at respective temperatures) in order to measure formation potential of a water sample for a future, selective age of the sample.

As noted earlier, various embodiments of an in-situ DBP detection mechanism can be used to generate formation potential measurements for DBPs, that is, an expectation as to the concentration of DBPs that might result from a given water sample at a future, defined age, given certain assumptions. In order to associate such measurements with corresponding age assumptions, it is advantageous to map data in advance that corresponds the specific heat or other profile used to artificially age the sample, in a manner such that the aging process accurately reflects the underlying assumptions. While the underlying assumptions can reflect any desired parameter, in one embodiment, this mapping process is used to correlate time of aging and average temperature of the water sample during the assumed aging process with a specific temperature profile or set of temperatures/heating times; with such a mapping established a priori and provided to software that performs the formation potential measurement, the artificial aging process can be performed so as to measure formation potential for a selective age (e.g., "72 hours"). FIG. 7 is used to discuss this mapping function.

More particularly, numeral 701 depicts a mapping process that can be performed for a range of ages and temperature assumptions, with the goal being to establish parameters that permit the real-time or near real-time measurement of DBP formation potential assuming a selective age and a selective average temperature during aging. In one embodiment, these selective values can be implied—for example, a heat profile used to artificially age a sample can be structures such that measurements already represent formation potential corresponding to, e.g., "72 hours at 72° F." In other embodiments, one or more programmable parameters is received in association with the formation potential prediction process and used to dial in a specific temperature profile that will then be applied in the real-time or near real-time DBP aging and measurement process.

To develop the mapping, per numeral 703, a relatively large sample of water, sufficient to source multiple measurements according to different, respective heat profiles is first drawn from water supply. The water sample is used in two types of measurement processes 705 and 707. In the first measurement process 705, a value in a range of temperatures and a value in a range of heating durations is selected (50-70° C. and 30-60 minutes for one embodiment), and this amount of heating is then applied to artificially age the specific measurement, and the resulting formation potential measurement is recorded (i.e., written to digital memory); the process is then repeated on a stepped basis for different temperatures and heating duration, such that measurement data for the same sample is obtained for values spanning each range (i.e., heat and time). Preferably, the measurements are completed in short duration and are performed successively or in parallel (such that actual, un-accelerated water aging does not affect results), and preferably for multiple different water samples of differing constituency to ensure statistical accuracy of results). In parallel with each measurement, a portion of the water sample is aged 707 for a period of time in a range of ages 709 on a similar, stepped basis (e.g., 6 hours, 12 hours, 18 hours . . . , 72 hours, etc.) at an assumed temperature (e.g., 72° F.), with each portion then being measured 711 for actual concentration of the DBP at issue once the particular age has been reached. The various measurements are then correlated 713 so as to link which heat treatments yield accelerated aging measurement results which closely align to measurements resulting from a specific age of the water sample, and a mapping is developed 715. This mapping is thereafter stored in processor accessible memory 717 and, as necessary or appropriate, is provided to or used to establish artificial aging parameters for an in-situ DBP detection mechanism 721, for "in-line" or "on-line" measurement of water in real-time or near real-time 723. In one embodiment, this task can be effectuated simply by programming desired heating and duration parameters into such an in-situ DBP detection mechanism such that formation potential measurements implicitly correspond to a selective (but assumed) age and average water temperature; by contrast, in other embodiments, as represented by numerals 725 and 726, the selective age and/or temperature can also be used to dynamically vary heating temperatures and/or duration, e.g., they can be programmably-received prior to measurement or at the time of measurement, or as part of an ad hoc formation potential measurement command. Whichever mechanism is used, the result of in-line measurement is then a predictive formation potential corresponding to a future time t, per numeral 727.

Reflecting on the various principles discussed above, techniques provided by this disclosure provide for accurate DBP prediction at various points in a water distribution system. In one embodiment, DBP measurements can be combined with other data (including measurements for other sources, and environmental and other variables) to develop a precise prediction of DBP presence a point that is downstream (i.e., time-wise or position-wise) in the water distribution process. In another embodiment, formation potential can be measured in real-time or near real-time and then supplied for use in managing water quality. In one implementation, these techniques can be practiced by a single device or detection mechanism (or by software), while in another implementation, they can be implemented by a network, or otherwise on a remote basis. Any such embodiment may optionally include support for taking, automated reactions (such as alerts and/or automated machine control) in response to the various measurements or predictions. As should be apparent from the foregoing, the disclosed techniques provide for significant improvement in the ability of water supplies to understand the effects that a given water supply or treatment process will have on water delivery at any point in time or in a water distribution process, and to manage water delivery accordingly, improving safety, efficiency and cost. Once again, all techniques can be implemented in-situ on a remote, calendared or ad-hoc basis, with equipment and software configured to perform sample extraction, measurement, cleaning, reporting of results and calibration, all on a fully automated basis.

Various alternatives to the foregoing techniques will readily occur to those having skill in the art. To pick just a few examples, techniques mentioned above may be applied using other types of detected optical activity (e.g., other than change in visible color intensity), and halohydrocarbon extraction may be accomplished using mechanisms other than an adsorbent medium. To pick another example, the method of business described above may be applied with or without modified Fujiwara-type chemistry. Many other variations also exist. Accordingly, the foregoing discussion is intended to be illustrative only; other designs, uses, alternatives, modifications and improvements will also occur to those having skill in the art which are nonetheless within the spirit and scope of the present disclosure, which is limited and defined only by the following claims and equivalents thereto.

I claim:

1. A method of estimating future build-up of at least one disinfection by-product (DBP) in water from a water supply, said method comprising:
controlling an actuator on an intermittent basis to automatically draw a sample of water from the water supply;
automatically transferring the sample to a vessel and heating the sample for a period of time, where both a temperature of the heating and the period of time of the heating are selected so as to simulate aging of the sample according to a selective age that has been correlated in advance with expected formation of the at least one DBP, given a normative amount of disinfection agent present in the water, and where the heating of the sample is to cause deliberate formation of the at least one DBP in the sampled water from un-neutralized disinfection agent present in the sampled water;
following heating, passing the sample through a transfer mechanism to extract the at least one DBP and to transfer the extracted at least one DBP to a second medium of known volume;
transferring the second medium of known volume to a measurement device, and measuring concentration of the at least one DBP in the second medium with the measurement device to generate at least one result; and
estimating the future build-up dependent on the at least one result;
wherein
the measuring of the concentration comprises initiating a reaction in which a pyridine-based substance is added to the second medium of known volume, measuring a color that is dependent on the concentration, and identifying the concentration dependent on the measured color, and
the controlling, the automatically transferring and heating, the passing, the transferring to the second medium and measuring and the estimating are each automated steps of a sequence for each sample performed on the intermittent basis under the control of one or more processors.

2. The method of claim 1, wherein the at least one DBP comprises a trihalomethane (THM), wherein initiating the reaction comprises introducing a predetermined volume of an organic developing agent to the second medium, and wherein measuring the color comprises measuring color in the second medium at a predetermined time following the introducing of the predetermined volume of the organic developing reagent to the second medium.

3. The method of claim 2, wherein the method comprises performing the measuring of the color at least twice, at different times relative to initiation of the reaction, to thereby generate two different color measurements, and wherein the one or more processors are to automatically generate results representing concentrations of at least two different THM species depending on the at least two different color measurements.

4. The method of claim 2, wherein the organic developing reagent is a pyridine derivative.

5. The method of claim 1, wherein the method further comprises, following the measuring of the concentration, renewing the transfer mechanism and the measurement device to remove residual DBP presence from a prior sample.

6. The method of claim 1, wherein:
the method further comprises performing a spike test using the measurement device; and
the one or more processors are to, as part of the spike test,
cause the automated addition of a predetermined quantity of the at least one DBP to the sample,
measure DBP concentration dependent on the sample and the predetermined quantity, and
compare a test result to a predetermined value to calibrate the measurement device.

7. The method of claim 1, wherein the method further comprises storing a value dependent on the at least one result in processor-accessible memory together with a time stamp corresponding to a time when the sample was drawn.

8. The method of claim 1, wherein the method further comprises transmitting (1) a value dependent on the at least one result via a wide area network using a transmission control protocol, for storage of the value in processor-accessible memory, together with a time stamp corresponding to a time when the sample was drawn from the water supply, and (2) information identifying an associated measurement source.

9. The method of claim 1, wherein the method further comprises storing a prediction of the future build-up of the at least one DBP in processor-accessible memory, together with a time stamp corresponding to a time when the sample was drawn.

10. The method of claim 1, wherein:
the estimating further comprises determining a value of at least one variable selected from the group of a water temperature, an atmospheric temperature, a date, a day of the week, a month, a season, an average age of water at a point in a water distribution network, and a flow rate; and
the estimating is performed in dependence on the value of the at least one variable, the at least one result, and the selective age.

11. The method of claim 1, wherein:
the estimating further comprises retrieving coefficients of a prediction algorithm from non-transitory processor-accessible storage;
the estimating is performed in dependence on the coefficients and values of variables respective to the coefficients; and
the method further comprises
receiving data representing measurement of concentration of the at least one DBP in water from the water supply which has been stored for a period corresponding to the selective age, and
updating the coefficients in response to a regression performed in dependence on the data.

12. The method of claim 11, wherein the actuator, the vessel and the measurement device are each part of an in-situ mechanism adapted to monitor water from the water supply for DBPs, and wherein the one or more processors are further to control the updating of the coefficients.

13. The method of claim 1, wherein the water supply comprises a potable water supply.

14. The method of claim 1, wherein:
estimating the future build-up further comprises collecting results from respective measurements of water drawn from the water supply at different points in time, each of said respective measurements obtained from the controlling, the automatically transferring, the passing, the transferring to the second medium and measuring and the estimating, as applied to a respective water sample drawn from the water supply; and
the estimating of the future build-up is performed in dependence on the collected results, such that the estimated future build-up corresponds to an accumulation of water provided at the different points in time from the water supply.

15. The method of claim 1, further comprising:
comparing the estimated future build-up of the DBP with at least one threshold; and
responsive to the comparing, causing the one or more processors to initiate at least one automated machine action.

16. The method of claim 15, wherein:
the at least one automated machine action comprises automatically generating, responsive to the comparing, one of
an email message operable to convey information representing the at least one result to a predetermined email address,
a voice mail message operable to convey information representing the at least one result to a predetermined, specific destination, and
a control value to be applied to at least one electromechanically-actuated water management process; and
the one or more processors are to initiate the at least one automated machine action by transmitting via a wide area network the email message, voice mail message or control value to a predetermined network address.

17. The method of claim 1, wherein the method further comprises:
measuring presence of the at least one DBP in water samples having the normative amount of the at least one disinfection agent, following aging of those water samples by respective amounts of time;
measuring presence of the at least one DBP in a nonaged water sample having the normative amount of the at least one disinfection agent following heating of the nonaged water sample using the at least one of the temperature of the heating and the period of time of the heating; and
correlating the at least one of the temperature of the heating and the period of time of the heating with the selective age, dependent on a relationship between measured presence of the at least one DBP in the aged water samples the measured presence of the at least one DBP in the nonaged water sample following the heating.

18. The method of claim 1, wherein the method further comprises:
   receiving with the one or more processors information identifying the selective age; and
   using the received information to access a processor-accessible memory, the processor-accessible memory storing respective temperature profiles previously correlated with respective water ages, to select each of the temperature of the heating and the period of time according to the information identifying the selective age.

19. The method of claim 1, wherein the controlling and the automatic transferring are characterized as not including performance of a stabilization process to neutralize a disinfection agent present in the sample of water, if any.

20. The method of claim 1, wherein the method further comprises taking at least one action, dependent on the estimating of the future build-up, from the group of storing the at least one result in processor-accessible memory, causing provision of information dependent on the at least one result via a user interface device to at least one human operator, or reactively controlling a system that handles or treats the water.

21. An apparatus to estimate future build-up of at least one disinfection by-product (DBP) in water from a water supply, said apparatus comprising instructions stored on non-transitory machine-readable media, said instructions when executed to cause one or more processors to:
   control an actuator to, on an intermittent basis, automatically draw a sample of water from the water supply;
   automatically transfer each sample to a vessel and heat the sample for a period of time, where both a temperature of the heating and the period of time of the heating are selected so as to simulate aging of the sample according to a selective age that has been correlated in advance with expected formation of the at least one DBP, given a normative amount of disinfection agent present in the water, and where the heating of the sample is to cause deliberate formation of the at least one DBP in the sampled water from un-neutralized disinfection agent present in the sampled water;
   cause passage of the sample following heating through a transfer mechanism to extract the at least one DBP and to transfer the extracted at least one DBP to a second medium of known volume;
   cause transfer of the second medium of known volume to a measurement device, and cause measurement of concentration of the at least one DBP in the second medium, with the measurement device, to generate at least one result; and
   calculate an estimate of the future build-up dependent on the at least one result;
   wherein the one or more processors are to cause measurement of the concentration by initiating a reaction in which a pyridine-based substance is added to the second medium of known volume, by controlling the measurement device so as to measure a color that is dependent on the concentration, and by identifying the concentration dependent on the measured color.

22. The apparatus of claim 21, wherein the instructions when executed are to cause the one or more processors to:
   receive information identifying the selective age; and
   use the received information to access a processor-accessible memory, the processor-accessible memory storing respective temperature profiles previously correlated with respective water ages, and to select each of the temperature of the heating and the period of time from the respective temperature profiles according to the information identifying the selective age.

23. The apparatus of claim 21, wherein the control and the automatic transferal are characterized as not including performance of a stabilization process to neutralize a disinfection agent present in the sample of water, DBPif any.

24. An apparatus to estimate future build-up of at least one disinfection by-product (DBP) in water from a water supply, said apparatus comprising circuitry, including one or more processors, to:
   automatically control an actuator, on an intermittent basis, to automatically draw a sample of water from the water supply;
   automatically cause transfer each sample to a vessel and heat the sample for a period of time, where both a temperature of the heating and the period of time of the heating are selected so as to simulate aging of the sample according to a selective age that has been correlated in advance with expected DBP formation given a normative amount of disinfection agent present in the water, and where the heating of the sample is to cause deliberate formation of the at least one DBP in the sampled water from un-neutralized disinfection agent present in the sampled water;
   automatically cause passage of the sample following heating through a transfer mechanism to extract the at least one DBP and to transfer the extracted at least one DBP to a second medium of known volume;
   automatically cause transfer the second medium of known volume to a measurement device, and measure concentration of the at least one DBP in the second medium with the measurement device to generate at least one result; and
   automatically calculate an estimate the future build-up dependent on the at least one result;
   wherein the circuitry is to cause measurement of the concentration by initiating a reaction in which a pyridine-based substance is added to the second medium of known volume, by controlling the measurement device so as to measure a color that is dependent on the concentration, and by identifying the concentration dependent on the measured color.

25. The apparatus of claim 24, wherein circuitry is further to:
   receive information identifying the selective age; and
   use the received information to access a processor-accessible memory, the processor-accessible memory storing respective temperature profiles previously correlated with respective water ages, and to select each of the temperature of the heating and the period of time from the respective temperature profiles according to the information identifying the selective age.

26. The apparatus of claim 24, wherein the control and the automatic transferal are characterized as not including performance of a stabilization process to neutralize a disinfection agent present in the sample of water, if any.

* * * * *